(12) United States Patent
Hadwiger et al.

(10) Patent No.: US 7,906,484 B2
(45) Date of Patent: Mar. 15, 2011

(54) COMPLEX FOR TRANSFERRING AN ANIONIC SUBSTANCE INTO A CELL

(75) Inventors: Philipp Hadwiger, Alenkunstadt (DE); Anke Geick, Bayreuth (DE)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 447 days.

(21) Appl. No.: 11/859,278

(22) Filed: Sep. 21, 2007

(65) Prior Publication Data

US 2009/0176710 A1 Jul. 9, 2009

Related U.S. Application Data

(60) Provisional application No. 60/846,193, filed on Sep. 21, 2006, provisional application No. 60/898,435, filed on Jan. 30, 2007.

(51) Int. Cl.
*A61K 38/00* (2006.01)
*C12N 15/00* (2006.01)
*C12N 5/071* (2010.01)
*C07K 5/00* (2006.01)
*C07K 7/00* (2006.01)
*C07K 16/00* (2006.01)
*C07K 17/00* (2006.01)

(52) U.S. Cl. ....... 514/13; 435/320.1; 435/366; 530/325; 530/326

(58) Field of Classification Search ........................ None
See application file for complete search history.

(56) References Cited

U.S. PATENT DOCUMENTS

| 5,525,711 | A | | 6/1996 | Hawkins | |
|---|---|---|---|---|---|
| 5,595,897 | A | | 1/1997 | Midoux et al. | |
| 5,741,772 | A | * | 4/1998 | Chang | 514/2 |
| 5,928,944 | A | | 7/1999 | Seth et al. | |
| 2002/0055174 | A1 | * | 5/2002 | Rittner et al. | 435/463 |
| 2009/0232882 | A1 | * | 9/2009 | Hickey et al. | 424/450 |
| 2009/0298772 | A1 | * | 12/2009 | Thirman | 514/12 |

FOREIGN PATENT DOCUMENTS

| EP | 1 161 957 | * 12/2001 |
|---|---|---|
| WO | WO 96/40958 | * 12/1996 |

OTHER PUBLICATIONS

Cooper et al. Peptide Mini-Vectors for Gene Delivery. Angew. Chem. Int. Ed. 1999. Vo. 38, No. 13/14, pp. 1949-1952.*
Robinson et al. Improvements in transfection efficiency and tests of RNA interference (RNAi) approaches in the protozoan parasite Leishmania. Mol. Biochem. Parasitology. 2003. vol. 128, pp. 217-228.*
Hengen. Purification of His-Tag fusion proteins from *Escherichia coli*. TIBS. 1995. vol. 20, pp. 285-286.*
PCT International Search Report and Written Opinion, PCT/US2007/079203, Sep. 22, 2008, 10 Pages.
PCT International Preliminary Report on Patentability, PCT/US2007/079203, Mar. 24, 2009, 6 Pages.

* cited by examiner

*Primary Examiner* — Marcela M Cordero Garcia
(74) *Attorney, Agent, or Firm* — Fenwick & West LLP

(57) ABSTRACT

The present invention relates to compositions and methods for the delivery of an anionic substance using complexes, comprising the anionic substance and a peptide. These complexes are useful for delivering said anionic substance into a cell, particularly in therapeutic applications.

20 Claims, No Drawings

COMPLEX FOR TRANSFERRING AN ANIONIC SUBSTANCE INTO A CELL

CROSS REFERENCE TO RELATED INVENTIONS

This application claims priority to U.S. Provisional Application No. 60/846,193, filed Sep. 21, 2006, and U.S. Provisional Application No. 60/898,435, filed Jan. 30, 2007. The entire contents of these application are hereby incorporated by reference in the present application.

FIELD OF THE INVENTION

The present invention relates to compositions and methods for the delivery of an anionic substance using complexes, comprising the anionic substance and a peptide. These complexes are useful for delivering said anionic substance into a cell, particularly in therapeutic applications.

BACKGROUND OF THE INVENTION

RNA interference (RNAi) is an evolutionarily conserved, sequence specific mechanism triggered by double stranded RNA (dsRNA) that induces degradation of complementary target single stranded mRNA and "silencing" of the corresponding translated sequences (McManus and Sharp, Nature Rev. Genet. 2002, 3:737; Mello and Donte, Nature 2004, 431:338; Meister and Tuschl, Nature 2004, 431:343; Sen and Blau, FASEB J. 2006, 20:1293).

Exploiting this mechanism has yielded a powerful tool to unravel the function and significance of hitherto unknown or uncharacterized genes in in vitro experiments (Hannon and Rossi, Nature 2004, 431:371; Westbrook et al., Cold Spring Harb Symp Quant Biol. 2005, 70:435): RNAi can be used to down-regulate or silence the transcription and translation of a gene product of interest; where said gene product is unknown or uncharacterized, the development of a certain phenotype can be used to determine the function and/or significance of the gene product. Great potential is also seen in harnessing the underlying cellular mechanisms for the therapy of human disease (Zhou et al., Curr Top Med Chem. 2006, 6:901): where said gene product is in any way associated with a disease or disorder by way of its overabundance, its down-regulation may be used in the prevention and/or therapy of the disease or disorder.

The triggering of RNAi by dsRNA requires the dsRNA to be localized in the cytoplasm and/or nucleus of the cell in which the target gene is to be silenced. To this end, the dsRNA may be introduced directly into the cell, e.g. by bringing the cells into contact with the dsRNA, whereupon the dsRNA is actively or passively internalized. Therein, the dsRNA may be large, e.g. comprising 100, 200, 400 or more base pairs. A large dsRNA will be processed in mammals by an RNAse III-like enzyme commonly called Dicer to smaller fragments of 21 to 23 base pairs. Alternatively, the dsRNA may be small, e.g. of the size of the Dicer products (dsRNAs of this size, e.g. having not more than 30 base pairs, are in the art often referred to as short interfering RNAs, or siRNAs). The small dsRNAs, be they a product of Dicer activity or directly introduced, are subsequently unwound by, and one strand of the small dsRNA is incorporated into, a protein complex termed RISC (RNA induced silencing complex). RISC then proceeds to cleave mRNAs having a sequence complementary to the RNA strand that was incorporated into RISC (Meister and Tuschl, Nature 2004, 431:343).

Alternatively, a nucleic acid molecule may be introduced into the cell encoding the dsRNA, whereupon the cell's own expression machinery produces the dsRNA which is the processed as set out above. Regardless of which method is chosen, in order to harness RNAi for any purpose in vitro and/or in vivo, a nucleic acid molecule must somehow be introduced into a cell. If RNA interference is to live up to its potential, the process of introducing the nucleic acid molecule should disrupt the natural functions of the cell as little as possible, particularly where the cell is part of a living organism.

This problem is shared by, for example, many procedures in genetic engineering, as well as gene therapy. Numerous solutions have been proposed, none of which is so far fully satisfactory.

For example, viral vectors are relatively efficient delivery systems for large nucleic acids, but suffer from a variety of limitations, such as the potential for reversion to the wild type as well as immune response concerns. Furthermore, in in vivo applications, viral systems are rapidly cleared from the circulation, limiting transfection to "first-pass" organs such as the lungs, liver, and spleen. In addition, these systems induce immune responses that compromise delivery with subsequent injections.

As a result, nonviral gene delivery systems are receiving increasing attention (Worgall, et al., Human Gene Therapy 8:37 (1997); Peeters, et al., Human Gene Therapy 7:1693 (1996); Yei, et al., Gene Therapy 1: 192 (1994); Hope, et al., Molecular Membrane Biology 15:1 (1998)). For example, in 1990, Wolff et al. (1990, Science, 247, 1465-1468) have shown that injection of naked RNA or DNA, without any special delivery system, directly into mouse skeletal muscle, results in expression of a reporter gene within the muscle cells. Nevertheless, although these results indicate that nucleic acid by itself is capable of crossing the plasma membrane of certain cells in vivo, the efficiency of the transfection, and thereby of the gene expression, observed in most of the cell types remains very limited due, in particular, to the polyanionic nature of nucleic acids which limits their passage through negatively-charged cell membranes.

Other groups (see Rolland, 1998, Therapeutic Drug Carrier Systems, 15, 143-198 for a review) have proposed alternative synthetic systems using cationic lipids or cationic polymers in order to facilitate the introduction of anionic molecules such as nucleic acids into cells. These cationic compounds are capable of forming complexes with anionic molecules, thus tending to neutralize their negative charges and allowing to compact them in complexed form which favors their introduction into the cell. These non-viral delivery systems are, for example, based on receptor-mediated mechanisms (Perales et al., 1994, Eur. J. Biochem. 226, 255-266; Wagner et al., 1994, Advanced Drug Delivery Reviews, 14, 113-135), on polymer-mediated transfection such as polyamidoamine (Haensler et Szoka, 1993, Bioconjugate Chem., 4, 372-379), dendritic polymer (WO 95/24221), polyethylene imine or polypropylene imine (WO 96/02655), polylysine (U.S. Pat. No. 5,595,897 or FR 2 719 316) or on lipid-mediated transfection (Felgner et al., 1989, Nature, 337, 387-388) such as DOTMA (Felgner et al., 1987, PNAS, 84, 7413-7417), DOGS or Transfectam™ (Behr et al., 1989, PNAS, 86, 6982-6986), DMRIE or DORIE (Felgner et al., 1993, Methods 5, 67-75), DC-CHOL (Gao et Huang, 1991, BBRC, 179, 280-285), DOTAP™ (McLachlan et al., 1995, Gene Therapy, 2, 674-622), Lipofectamine™ or glycerolipid compounds (see for example EP 901 463 and WO98/37916).

These non-viral systems present special advantages with respect to large-scale production, safety, low immunogenicity, and capacity to deliver large fragments of DNA.

Besides, analyses have shown that a major pathway for intracellular delivery of these non-viral systems is internalization into vesicles by endocytosis. Endocytosis is the natural process by which eukaryotic cells ingest segments of the plasma membrane in the form of small endocytosis vesicles, i.e. endosomes, entrapping extracellular fluid and molecular material, e.g. nucleic acid molecules. In cells, these endosomes fuse with lysosomes which are specialized sites of intracellular degradation. The lysosomes are acidic and contain a wide variety of degradative enzymes to digest the molecular contents of the endosomal vesicles. After endocytosis the internalized material is thus still separated from the cytoplasm by a membrane and therefore is not available for performing its desired function. Actually, in most of the nucleic acids transfer approaches said desired function, i.e. the desired therapeutic effect, depends on their delivery at least into the cytoplasm (e.g. for RNA) or rather into the nucleus of the cell (e.g. for DNA encoding a polypeptide or antisense oligonucleotides) where their functional effect can occur. Consequently, the internalized nucleic acid accumulation into endosomal vesicles strongly reduces the efficiency of nucleic acid functional transfer to the cell, and therefore the efficiency of gene therapy (Zabner et al., 1995, J. Biol. Chem., 270, 18997-19007).

Accordingly, the efficient delivery to and expression of genetic information within the cells of a living organism depend both on the capability of the delivery system to transfer the nucleic acid molecule into the cell and on its capability to promote nucleic acid escape from endosomal retention and degradation.

Once the delivery system has been taken up by cells via endocytosis, it must escape from the endosomal compartment for being localized in the cytoplasm or to migrate to the nucleus. The general strategy is to promote endosomolysis, e.g. by using fusogenic or membranolytic/endosomolytic peptides (see Mahato et al., 1999, Current Opinion in Mol. Therapeutics, 1, 226-243).

Some microorganisms (e.g. viruses) are naturally internalized via receptor-mediated endocytosis and have developed systems for escaping from the above-mentioned endosomal degradation. Based on this natural aptitude, gene transfer systems have been proposed including the endosome-destabilizing activity of replication-defective adenovirus particles or rhinovirus particles which were either added to the transfection medium (Cotten et al., 1992, Proc. Natl. Acad. Sci. USA, 89, 6094-6098) or directly linked to the delivery complex (Wu et al., 1994, J. Biol. Chem., 269, 11542-11546; U.S. Pat. No. 5,928,944). Expression levels resulting from in vivo gene transfer with these systems, while promising, are still relatively low and further optimization is required. Additionally, synthetic systems have been generated. The best characterized synthetic peptides with fusogenic activity are derived from the first 23 amino acids of the N-terminal peptide of the HA2 subunit of influenza hemagglutinin (e.g. the INF peptide). At pH 7, this peptide preferentially assumes a random coil structure. At pH 5, an amphipathic alpha-helical conformation is favoured and the peptide becomes endosomolytic. Similarly, the synthetic peptide JTS-1 developed by Gottschalk et al. (1996, Gene Therapy, 3, 448-457) starts with the INF sequence GLFEA followed by an optimized peptide sequence. This JTS-1 peptide was shown to be capable of lysing calcein containing phosphatidylcholine liposomes at pH 5, more efficiently than at a pH 7.

However, the intracellular delivery of nucleic acids requires that said peptides combine their fusogenic activity with a nucleic acid complexing activity to form delivery complexes capable of transferring said nucleic acid into cells.

Some systems developed so far combine two distinct elements presenting said features (for example, WO 96/40958, WO 98/50078 or Gottschalk et al., 1996, Gene Therapy, 3, 448-457, Haensler & Szoka, 1993, Bioconjugate Chem., 4, 372-379). These two-components systems actually include peptides which have specificity for endosomal pH due to acidic residues (glutamic and aspartic amino acids). At neutral pH, the negatively charged carboxylic groups destabilize the structure of these peptides; acidification of the carboxylic groups promotes multimerization of the peptides and/or membrane interaction leading to membrane destabilization and leakage. Wagner et al. (1999, Advanced Drug Delivery Reviews, 38, 279-289) have analyzed this pH specificity and have indicated that introduction of additional glutamic acids into peptides can enhance their pH specificity, and therefore their endosome disrupting property. However, said combined systems which retain the endosome disruptive properties of viral particles and are capable of associating with the nucleic acid molecule to form a complex must display a delicate balance between each distinct moieties (i.e. the nucleic acid-binding ligand and the synthetic membrane-destabilizing peptide) in order to promote intracellular nucleic acid transfer and to function under in vitro as well as in vivo conditions.

With the aim to propose a simplified system, Wyman et al. (1997, Biochemistry, 36, 3008-3017) developed a single-component system using a designed synthetic peptide, KALA, which can promote in vitro transfection of nucleic acid molecules and can cause membrane disruption. While positively charged hydrophilic lysine amino acid residues have been chosen to bind the nucleic acid molecule, glutamic amino acid residues are still maintained to provide the KALA peptide with pH specificity and thereby to guarantee its endosome disrupting property. Additionally, Gottschalk et al. (1996, Gene Therapy, 3, 448-457) have found that the disrupting activity of peptides is not the unique factor that determines gene transfer activity and that single amino acid substitutions in said peptide sequence can significantly decrease their disruptive property on the endosomal membrane, suggesting that these peptide systems require careful optimization at the risk of loosing at least one of the two required properties.

Further attempts at providing optimized delivery agents were undertaken by, for example, Kichler et al. (WO 02/096928) and Eccles and Muratowska (WO 04/007721). The latter proposed conjugating penetratin or transportan to siRNAs.

Rittner and Jacobs (WO 02/074794, EP 1161957) proposed slightly modified forms of the peptides developed by Gottschalk et al., supra, e.g. a peptide they termed ppTG20. ppTG20 corresponds to JTS-1, but with all glutamic acid residues replaced by arginines.

Pichon et al. (2001, Advanced Drug Delivery Reviews, 53, 75-94) demonstrated that improved nucleid acid cross-membrane transport capabilities may be imparted to certain peptides and amino acid polymers, e.g. poly-L-lysine, by substituting a number of amino acids by histidine, or adding histidyl residues as side chain modifications, respectively.

The available nucleic acid delivery systems are not yet satisfactory in terms of safety and/or efficiency for their utilization in in vitro experimental applications and/or human diagnosis and therapy, and require further optimization.

The technical problem underlying the present invention is the provision of improved methods and means for the delivery into cells of anionic substances, preferably of nucleic acid molecules, which are useful in vitro and in vivo, preferably for human therapy. This problem has been solved by the provision of the embodiments as characterized herein below and in the claims.

SUMMARY OF THE INVENTION

Accordingly, the present invention relates to a peptide comprising or consisting of the amino acid sequence GLFXALLXLLXSLWXLLLXAZ$_1$Z$_2$Z$_3$Z$_4$ (SEQ ID NO:1), wherein each X is independently E, R, A, I, L, F, P, W, V, N, C, Q, G, S, T or Y, and wherein each of Z$_1$, Z$_2$, Z$_3$, and Z$_4$, is independently H, K, R, or Q. Preferably, each X is independently E or R, and each of Z$_1$, Z$_2$, Z$_3$, and Z$_4$, is independently H, K, R, or Q. More preferably, each X is independently E or R, and each of Z$_1$, Z$_2$, Z$_3$, and Z$_4$, is independently H, K, or R. Yet more preferably, each X is independently E or R, and each of Z$_1$, Z$_2$, Z$_3$, and Z$_4$, is H. Most preferably, the peptide comprises or consists of one of the amino acid sequences SEQ. ID NO:3 to SEQ. ID NO:8.

In another aspect of the invention, a peptide is provided that may be derived from the formula GLFRALLRLLRSLWR-LLLRA (SEQ ID NO:2) by at least one of the following substitutions: G1→R, L18→R, S12→R, L7→R, G1→H, L18→H, S12→H, L7→H, A5→H, R15→H, L16→H, L18→S, L16→S, F3→Y, L2→A, L6→A, L16→A, L18→A, L9→A, and or by adding 4 or more, 5 or more, or 10 or more histidine residues to the N- and/or C-terminus, and preferably to the C-terminus. Preferably, such a peptide of the invention is one of AP-0, AP-1, AP-1, AP-2, AP-3, AP-4, AP-5, AP-6, AP-7, AP-8, AP-9, AP-10, AP-11, AP-12, AP-13, AP-14, AP-15, AP-16, AP-17, AP-18, AP-19, AP-20, AP-21, AP-22, AP-23, AP-24, AP-25, AP-26, AP-30, AP-32, or AP-34, as described hereinbelow. More preferably, the peptide is AP-1, AP-4, or AP-10.

The peptide which has been identified in connection with the present invention is capable of causing cell membrane disruption, capable of binding to an anionic substance, in particular a nucleic acid molecule, capable of enhancing the transfer of said anionic substance into a cell and, eventually, capable of enhancing the inhibition of a target gene by said anionic substance, wherein the anionic substance is an antisense oligonucleotide, ribozyme, aptamer, and/or mediates RNA interference. Alternatively, and optionally, wherein the anionic substance is a nucleic acid and encodes genetic information that may be expressed in the cell, it may enhance the expression of the genetic information from the nucleic acid.

In another aspect of the invention, a composition is provided, comprising a complex of (i) at least one peptide of the invention and (ii) at least one anionic substance of interest. The molar ratio (peptide):(anionic substance) in the complex may be between 1:100 and 100:1, preferably 1:1 and 20:1, more preferably between 5:1 and 15:1, most preferably between 8:1 and 13:1, and specifically 8:1, 10:1, or 12:1. Preferably, the anionic substance is a nucleic acid, DNA, mRNA, single stranded RNA (ssRNA), antisense oligonucleotide (AON), ribozyme, aptamer, or a dsRNA, particularly a dsRNA that mediates RNA interference, e.g. is an siRNA or shRNA. Preferably, wherein the nucleic acid encodes genetic information that may be expressed in the cell, the product of the expression of the comprised genetic information is an mRNA, single stranded RNA (ssRNA), antisense oligonucleotide (AON), ribozyme, aptamer, or a dsRNA, particularly a dsRNA that mediates RNA interference, e.g. is an siRNA or shRNA, as defined below. More preferably, the anionic substance is itself an mRNA, single stranded RNA (ssRNA), antisense oligonucleotide (AON), ribozyme, aptamer, or a dsRNA, particularly a dsRNA that mediates RNA interference, e.g. is an siRNA or shRNA.

Preferably, the complex further comprises: (iii) at least one ligand capable of cell-specific and/or nuclear targeting; and/or (iv) at least one further peptide capable of causing membrane disruption, and/or (v) at least one cationic compound selected from the group consisting of: cationic lipids and cationic polymers, and/or (vi) a colipid. Optionally, the composition further comprises a pharmaceutical carrier, making it a pharmaceutical composition.

In another aspect of the invention, a method for the manufacture of the above composition is provided, comprising the steps of (a) contacting at least one peptide of the present invention with an anionic substance of interest, and (b) recovering said complex, optionally after a purification or selection step. Optionally the method further encompasses the step of formulating the complex with a pharmaceutical carrier. Further preferred embodiments of the instant method are as provided for other inventive aspects above.

In another aspect of the invention, a method to introduce an anionic substance into a cell is provided, comprising the steps of: (1) contacting the anionic substance with a peptide of the invention, such that a complex is formed, and (2) contacting said cell with said complex. Preferred embodiments of the instant method are as provided for other inventive aspects above.

In yet another aspect of the invention, a method to treat a subject is provided, comprising the step of: administering to the subject a pharmaceutical composition of the invention, as described above. Preferably, the subject is a vertebrate, more preferably a mammal, yet more preferably a human. Other preferred embodiments of the instant method are as provided for other inventive aspects above.

In another aspect of the invention, a cell comprising a peptide of the invention, optionally in a complex with an anionic substance, is provided. Preferred embodiments of the instant cell are as provided for other inventive aspects above.

BRIEF DESCRIPTION OF DRAWINGS

No drawings are presented.

DETAILED DESCRIPTION OF THE INVENTION

The term "peptide", "amino acid residues" and "acidic amino acid residues" as used herein are intended to have the same meaning as commonly understood by one of ordinary skill in the art. Preferably, "peptide" refers to a polymer of amino acid residues that is less than 50 residues in length, more preferably less than 30 residues in length and most preferably less than 25 residues in length. In a preferred embodiment, the peptide of the present invention has a molecular weight of less than 5 kD and most preferably of less than 3 kD. Peptides according to the invention may be produced de novo by synthetic methods or by expression of the appropriate DNA fragment by recombinant DNA techniques in eukaryotic or prokaryotic cells. In a special embodiment, said peptide contains one or more non-hydrolyzable chemical moieties in place of those which exist in naturally occurring peptides, such as carboxyl moieties. In that special case, the naturally hydrolyzable moities are replaced by non-hydrolizable ones such as for example methylene moieties. The present invention also encompasses analogs of the above described peptide, wherein at least one amino acid is replaced by another amino acid having similar properties, including retro or inverso peptides (WO95/24916). Additionally, the ligand moiety in use in the invention may include modifications of its original structure by way of substitution or addition of chemical moieties (e.g. glycosylation, alkylation, acetylation, amidation, phosphorylation, addition of sulfhydryl groups and the like). The present invention also contemplates modifications that render the peptides of the invention detectable. For this purpose, the peptides of the invention can be modified with a detectable moiety (i.e. a scintigraphic, radioactive, a fluorescent moiety, an enzyme, a dye label and the like). Suitable radioactive labels include but are not limited to $^{99}$Tc, $^{123}$I and $^{111}$In. Such labels can be attached to the peptide of the invention in a known manner, for example via a cysteine residue. Other techniques are described elsewhere and are familiar to the skilled person. The labeled peptides of the invention may be used for diagnostic purposes (e.g. imaging of tumoral cells, of transformed cells, and the like). In a preferred embodiment, the peptide is a cationic peptide.

The peptides of the invention can be generated by any method known to the skilled person. For example, the peptides of the invention can be synthesized, e.g. by any of the methods described in, for example, M. Bodanszky & A. Bodanszky, "The Practice of Peptide Synthesis", 2. Auflage, Springer-Verlag, Heidelberg, Germany, 1994, M. Bodanszky, "Principles of Peptide Synthesis", Springer-Verlag, Heidelberg, Germany, 1984, or "Fmoc Solid Phase Synthesis", Chan, W. C., White, P. D. (Edrs.), Oxford University Press, Oxford, UK, 2000.

The term "peptide capable of causing membrane disruption" as used herein refers to a peptide which is capable of interacting with a membrane, particularly with a cellular membrane, and more particularly with an endosomal and/or lysosomal membrane, in such a manner that said interaction results in destabilizing and/or leaking of the membrane, and particularly in freeing the contents of the endosomes. Preferably, said interaction results in freeing the endosome and/or lysosome contents into the cytoplasm of the cell. The membrane disrupting property of the peptide can be easily measured for example by the method described in Olson et al., Biochim. Biophys. Acta 1979, 557:19-23, or in EP 1161957. The term "membrane" as used herein is intended to have the same meaning as commonly understood by one of ordinary skill in the art. Generally, it designates a mono or bi layer consisting mainly of lipids, and eventually contains proteins. Included are natural (e.g. membrane of the cells) and synthetic (e.g. liposomal) membranes. Preferred membranes are natural membranes such as for example cellular membranes, endosomal or lysosomal membranes, trans-Golgi network membranes, virus membranes, and nuclear membranes.

The terms "capable of enhancing the transfer of said anionic substance", "capable of enhancing the inhibition of a target gene", and "enhance the expression of genetic information" as used herein refer to the capability of the peptide to increase the level of transfer of the anionic substance into the target cells, and or to increase the desired effect of the anionic substance to be transferred into the target cell as compared to contacting the target cell with the anionic substance alone, or in combination with another commonly used transfection agent or method, e.g. lipofectamine™ or electroporation. E.g., where the anionic substance is an siRNA, the complex of the inventive peptide with the siRNA achieves a greater level of target gene inhibition than the siRNA alone, or optionally in combination with lipofectamine™, at the same concentration of the siRNA, or the same level of inhibition at a lower concentration of the siRNA.

In a special embodiment, the peptide of the invention is modified by addition of at least one cysteine residue at its N- and/or C-terminal extremities. This modification allows for example the formation of di-, tri- or multimeric association of peptides of the present invention. Said association of modified peptides can be linear or cyclized.

In a preferred embodiment, the peptide of the invention may comprise, or consist of the amino acid sequence GLFXALLXLLXSLWXLLLXAZ$_1$Z$_2$Z$_3$Z$_4$ (SEQ ID NO:1), wherein each X is independently glutamic acid (Glu or E), arginine (Arg or R), alanine (Ala or A), Isoleucine (Ile or I), Leucine (Leu or L), phenylalanine (Phe or F), proline (Pro or P), tryptophan (Trp or W), valine (Val or V), asparagines (Asn or N), cysteine (Cys or C), glutamine (Gln or Q), glycine (Gly or G), serine (Ser or S), threonine (Thr or T) or Tyrosine (Tyr or Y), and wherein each of Z$_1$, Z$_2$, Z$_3$, and Z$_4$, is independently histidine (His or H), lysine (Lys or K), arginine (Arg or R), or glutamine (Gln or Q). Preferably, each X is independently E or R, and each of Z$_1$, Z$_2$, Z$_3$, and Z$_4$ is independently H, K, R, or Q. More preferably, each X is independently E or R, and each of Z$_1$, Z$_2$, Z$_3$, and Z$_4$ is independently H, K, or R. Yet more preferably, each X is independently E or R, and each Z is H.

In another preferred embodiment, the peptide of the invention may comprise, or consist of, an amino acid sequence selected among the following:

```
ppTGHis (24-mer)
GLFRALLRLLRSLWRLLLRAHHHH       (SEQ ID NO: 3)

ppTGArg (24-mer)
GLFRALLRLLRSLWRLLLRARRRR       (SEQ ID NO: 4)

ppTGLys (24-mer)
GLFRALLRLLRSLWRLLLRALLLL       (SEQ ID NO: 5)

ppTGEHis (24-mer)
GLFEALLELLESLWELLLEAHHHH       (SEQ ID NO: 6)

ppTGEArg (24-mer)
GLFEALLELLESLWELLLEARRRR       (SEQ ID NO: 7)

ppTGELys (24-mer)
GLFEALLELLESLWELLLEALLLL       (SEQ ID NO: 8)
```

In another aspect of the invention, a peptide is provided that may be derived from the formula GLFRALLRLLRSLWR-LLLRA (SEQ ID NO:2) by at least one of the following substitutions: G1→R, L18→R, S12→R, L7→R, G1→H, L18→H, S12→H, L7→H, A5→H, R15→H, L16→H, L18→S, L16→S, F3→Y, L2→A, L6→A, L16→A, L18→A, L9→A, and or by adding 4 or more, 5 or more, or 10 or more histidine residues to the N- and/or C-terminus, and preferably to the C-terminus. Preferably, such a peptide of the invention is one of AP-0, AP-1, AP-1, AP-2, AP-3, AP-4, AP-5, AP-6, AP-7, AP-8, AP-9, AP-10, AP-11, AP-12, AP-13, AP-14, AP-15, AP-16, AP-17, AP-18, AP-19, AP-20, AP-21, AP-22, AP-23, AP-24, AP-25, AP-26, AP-30, AP-32, or AP-34, as described hereinbelow. More preferably, the peptide is AP-1, AP-4, or AP-10.

In another aspect the invention provides a composition comprising: (i) at least one peptide of the present invention, (ii) at least one anionic substance of interest.

"Anionic substance of interest" designates a negatively-charged molecule without a limitation of the number of charges. Preferably, said molecule can be selected from the group consisting of proteins and nucleic acid molecules. According to a preferred embodiment, said anionic substance of interest is a nucleic acid molecule.

The term "nucleic acid" or "nucleic acid molecule" as used in the scope of the present invention means a DNA or RNA or a fragment or combination thereof, which is single- or double-stranded, linear or circular, natural or synthetic, modified or not (see U.S. Pat. Nos. 5,525,711, 4,711,955, 5,792,608 or EP 302 175 for modification examples) without size limitation. It may, inter alia, be a genomic DNA, a cDNA, an mRNA, an antisense RNA, a ribozyme, an siRNA, an shRNA, or a DNA encoding such RNAs. The terms "polynucleotide", "nucleic acid molecule" and "nucleic acids" are synonyms with regard to the present invention. The nucleic acid may be in the form of a linear or circular polynucleotide, and preferably in the form of a plasmid. The nucleic acid can also be an oligonucleotide which is to be delivered to the cell, e.g., for antisense, ribozyme, or RNA interference functions. According to the invention, the nucleic acid is preferably a naked polynucleotide (Wolff et al., Science 247 (1990), 1465-1468) or is formulated with at least one compound such as a polypeptide, preferably a viral polypeptide, or a cationic lipid, or a cationic polymer, or combination thereof, which can participate in the uptake of the polynucleotide into the cells (see Ledley, Human Gene Therapy 6 (1995), 1129-1144 for a review) or a protic polar compound (examples are provided below in the present application or in EP 890362).

Preferably, said nucleic acid molecule includes at least one encoding gene sequence of interest (i.e. a transcriptional unit) that can be transcribed and translated to generate a polypeptide of interest and the elements enabling its expression (i.e. an expression cassette). If the nucleic acid contains this proper genetic information when it is placed in an environment suitable for gene expression, its transcriptional unit will thus express the encoded gene product. The level and cell specificity of expression will depend to a significant extent on the strength and origin of the associated promoter and the presence and activation of an associated enhancer element. Thus in a preferred embodiment, the transcriptional control element include the promoter/enhancer sequences such as the CMV promoter/enhancer. However, those skilled in the art will recognize that a variety of other promoter and/or enhancer sequences are known which may be obtained from any viral, prokaryotic, e.g. bacterial, or eukaryotic organism, which are constitutive or regulatable, which are suitable for expression in eukaryotic cells, and particularly in target cells. More precisely, this genetic information necessary for expression by a target cell comprises all the elements required for transcription of said gene sequence (if this gene sequence is DNA) into RNA, preferably into mRNA, and, if necessary, for translation of the mRNA into a polypeptide. Promoters suitable for use in various vertebrate systems are widely described in literature. Suitable promoters include but are not limited to the adenoviral Ela, MLP, PGK (Phospho Glycero Kinase; Adra et al. Gene 60 (1987) 65-74; Hitzman et al. Science 219 (1983) 620-625), RSV, MPSV, SV40, CMV or 7.5k, the vaccinia promoter, inducible promoters, MT (metallothioneine; Mc Ivor et al., Mol. Cell Biol. 7 (1987), 838-848), alpha-1 antitrypsin, CFTR, immunoglobulin, alpha-actin (Tabin et al., Mol. Cell Biol. 2 (1982), 426-436), SR (Takebe et al., Mol. Cell. Biol. 8 (1988), 466-472), early SV40 (Simian Virus), RSV (Rous Sarcoma Virus) LTR, TK-HSV-1, SM22 (WO 97/38974), Desmin (WO 96/26284) and early CMV (Cytomegalovirus; Boshart et al. Cell 41 (1985) 521), etc. Alternatively, one may use a synthetic promoter such as those described in Chakrabarti et al. (1997, Biotechniques 23, 1094-1097), Hammond et al. (1997, J. Virological Methods 66, 135-138) or Kumar and Boyle (1990, Virology 179, 151-158) as well as chimeric promoters between early and late poxviral promoters. Alternatively, promoters can be used which are active in tumor cells. Suitable examples include but are not limited to the promoters isolated from the gene encoding a protein selected from the group consisting of MUC-1 (overexpressed in breast and prostate cancers; Chen et al., J. Clin. Invest. 96 (1995), 2775-2782), CEA (Carcinoma Embryonic Antigen; overexpressed in colon cancers; Schrewe et al., Mol. Cell. Biol. 10 (1990), 2738-2748), tyrosinase (overexpressed in melanomas; Vile et al., Cancer Res. 53 (1993), 3860-3864), ErbB-2 (overexpressed in breast and pancreas cancers; Harris et al., Gene Therapy 1 (1994), 170-175) and alpha-foetoprotein (overexpressed in liver cancers; Kanai et al., Cancer Res. 57 (1997), 461-465) or combinations thereof. The early CMV promoter is preferred in the context of the invention.

The nucleic acid can also include intron sequences, targeting sequences, transport sequences, sequences involved in replication or integration. Said sequences have been reported in the literature and can readily be obtained by those skilled in the art. The nucleic acid can also be modified in order to be stabilized with specific components, for example spermine. It can also be substituted, for example by chemical modification, in order to facilitate its binding with specific polypeptides such as, for example the peptides of the present invention. According to the invention, the nucleic acid can be homologous or heterologous to the target cells into which it is introduced.

In a preferred embodiment, the nucleic acid contains at least one gene sequence of interest encoding a gene product which is a therapeutic molecule (i.e. a therapeutic gene). A "therapeutic molecule" is one which has a pharmacological or protective activity when administered appropriately to a patient, especially a patient suffering from a disease or illness condition or who should be protected against this disease or condition. Such a pharmacological or protective activity is one which is expected to be related to a beneficial effect on the course or a symptom of said disease or said condition. When the skilled man selects in the course of applying the present invention a gene encoding a therapeutic molecule, he generally relates his choice to results previously obtained and can reasonably expect, without undue experiment other than practicing the invention as claimed, to obtain such pharmacological property. According to the invention, the sequence of interest can be homologous or heterologous to the target cells into which it is introduced. Advantageously said sequence of interest encodes all or part of a polypeptide, especially a therapeutic or prophylactic polypeptide giving a therapeutic or prophylactic effect. A polypeptide is understood to be any translational product of a polynucleotide regardless of size, and whether glycosylated or not, and includes peptides and proteins. Therapeutic polypeptides include as a primary example those polypeptides that can compensate for defective or deficient proteins in an animal or human organism, or those that act through toxic effects to limit or remove harmful cells from the body. They can also be immunity conferring polypeptides which act as an endogenous antigen to provoke a humoral or cellular response, or both.

The following encoding gene sequences are of particular interest. For example genes coding for a cytokine (α-, β-, or γ-interferon (INF), interleukine (IL), in particular IL-2, IL-6, IL-10 or IL-12, a tumor necrosis factor (TNF), a colony stimulating factor (such as GM-CSF, C-CSF, M-CSF), an immunostimulatory polypeptide (such as B7.1, B7.2, CD40, CD4, CD8, ICAM and the like), a cell or nuclear receptor, a receptor ligand (such as fas ligand), a coagulation factor (such as FVIII, FIX), a growth factor (such as Transforming Growth Factor TGF, Fibroblast Growth Factor FGF and the like), an enzyme (such as urease, renin, thrombin, metalloproteinase, nitric oxide synthase NOS, SOD, catalase), an enzyme inhibitor (such as α-1-antitrypsine, antithrombine III, viral protease inhibitor, plasminogen activator inhibitor PAI-1), the CFTR protein, insulin, dystrophin, an MHC antigen (Major Histocompatibility Complex) of class I or II or a polypeptide that can modulate/regulate the expression of one or more cellular genes, a polypeptide capable of inhibiting a bacterial, parasitic or viral infection or its development (such as antigenic polypeptides, antigenic epitopes, transdominant variants inhibiting the action of a native protein by competition), an apoptosis inducer or inhibitor (such as Bax, Bcl2, BclX), a cytostatic agent (such as p21, p16, Rb), an apolipoprotein (such as ApoAI, ApoAIV, ApoE), an inhibitor of angiogenesis (such as angiostatin, endostatin), an angiogenic polypeptide (such as family of Vascular Endothelial Growth Factors VEGF, FGF family, CCN family including CTGF, Cyr61 and Nov), an oxygen radical scavenger, a polypeptide having an anti-tumor effect, an antibody, a toxin, an immunotoxin and a marker (such as beta-galactosidase, luciferase) or any other gene of interest that is recognized in the art as being useful for the treatment or prevention of a clinical condition. In view of treating a hereditary dysfunction, one may use a functional allele of a defective gene, for example a gene encoding factor VIII or IX in the context of haemophilia A or B, dystrophin (or minidystrophin) in the context of myopathies, insulin in the context of diabetes, CFTR (Cystic Fibrosis Transmembrane Conductance Regulator) in the context of cystic fibrosis. Suitable anti-tumor genes include but are not limited to those encoding an antisense RNA, a ribozyme, a cytotoxic product such as thymidine kinase of herpes-1 simplex virus (TK-HSV-1), ricin, a bacterial toxin, the expression product of yeast genes FCY1 and/or FUR1 having UPRTase (Uracile Phosphoribosyltransferase) and CDase (Cytosine Deaminase) activity respectively, an antibody, a polypeptide inhibiting cellular division or transduction signals, a tumor suppressor gene (p53, Rb, p73), a polypeptide activating host immune system, a tumor-associated antigen (MUC-1, BRCA-1, an HPV early or late antigen (E6, E7, L1, L2), optionally in combination with a cytokine gene. The polynucleotide can also encode an antibody. In this regard, the term "antibody" encompasses whole immunoglobulins of any class, chimeric antibodies and hybrid antibodies with dual or multiple antigen or epitope specificities, and fragments, such as F(ab)'$_2$, Fab', Fab including hybrid fragments and anti-idiotypes (U.S. Pat. No. 4,699,880). Advantageously said nucleic acid encodes all or part of a polypeptide which is an immunity conferring polypeptide and acts as endogenous immunogen to provoke a humoral or cellular response, or both, against infectious agents, including intracellular viruses, or against tumor cells. An "immunity-conferring polypeptide" means that said polypeptide when it is produced in the transfected cells will participate in an immune response in the treated patient. More specifically, said polypeptide produced in or taken up by macropinocyte cells such as APCs will be processed and the resulting fragments will be presented on the surface of these cells by MHC class I and/or II molecules in order to elicit a specific immune response.

The nucleic acid may comprise one or more gene(s) of interest. In this regard, the combination of genes encoding a suicide gene product and a cytokine gene (e.g. α-, β-, or γ-INF, interleukins, preferably selected among IL-2, IL-4, IL-6, IL-10 or IL-12, TNF factors, GM-CSF, C-CSF, M-CSF and the like), an immunostimulatory gene (e.g. B7.1, B7.2, ICAM) or a chimiokine gene (e.g. MIP, RANTES, MCP 1) is advantageous. The different gene expression may be controlled by a unique promoter (polycistronic cassette) or by independent promoters. Moreover, they may be inserted in a unique site or in various sites along the nucleic acid either in the same or opposite directions.

The encoding gene sequence of interest may be isolated from any organism or cell by conventional techniques of molecular biology (PCR, cloning with appropriate probes, chemical synthesis) and if needed its sequence may be modified by mutagenesis, PCR or any other protocol.

Where the nucleic acid is an RNA, it is preferably an mRNA, single stranded RNA (ssRNA), antisense oligonucleotide (AON), ribozyme, aptamer, or a dsRNA, preferably an siRNA or shRNA. "RNA", as used herein, shall refer to nucleic acids having predominantly RNA-like properties, e.g. having the ability to hybridize to a substantially complementary RNA, forming an A-type helix. As used herein, and unless otherwise indicated, the term "substantially complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing.

Generally, an RNA will consist mostly, or exclusively, of ribonucleotides, i.e. cytidine, adenosine, guanosine and uridine nucleosides interconnected by 5'-3'-monophosphate bridging groups. However, one or more, or all, nucleotides may be 2'-O-methyl ribonucleotides, or nucleotides not naturally occurring in RNA, for example, without limitation, deoxyribonucleotides, inosines, 2'-deoxy-2'-fluoro-, or 2'-O [(CH$_2$)$_n$O]$_m$CH$_3$ ribonucleotides, as long as the overall molecule retains predominantly RNA-like properties. In addition, or alternatively, the RNA may comprise modified internucleoside linkages, e.g. phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included. Further nucleotide modifications are well known to the skilled person and are encompassed by the present invention, e.g. those described in WO 03/070918 and U.S. Pat. Nos. 3,687,808; 4,469,863; 4,476,301; 4,845,205; 4,981,957; 5,023,243; 5,034,506; 5,118,800; 5,134,066; 5,166,315; 5,175,273; 5,177,195; 5,185,444; 5,188,897; 5,214,134; 5,216,141; 5,235,033; 5,264,423; 5,264,564; 5,276,019; 5,278,302; 5,286,717; 5,319,080; 5,321,131; 5,359,044; 5,367,066; 5,393,878; 5,399,676; 5,405,938; 5,405,939; 5,432,272; 5,434,257; 5,446,137; 5,453,496; 5,455,233; 5,457,187; 5,459,255; 5,466,677; 5,466,677; 5,466,786; 5,470,967; 5,476,925; 5,484,908; 5,489,677; 5,502,177; 5,514,785; 5,519,126; 5,519,134; 5,525,711; 5,536,821; 5,541,307; 5,541,316; 5,550,111; 5,552,540; 5,561,225; 5,563,253; 5,567,811; 5,571,799; 5,576,427; 5,587,361; 5,587,469; 5,591,722; 5,594,121; 5,596,086; 5,596,091; 5,597,909; 5,602,240; 5,608,046; 5,610,289; 5,610,300; 5,614,617; 5,618,704; 5,623,070; 5,625,050; 5,627,053; 5,633,360; 5,639,873; 5,646,265; 5,658,873; 5,663,312; 5,670,633; 5,677,437; 5,677,439; 5,681,941; 5,700,920; 5,750,692, all of which are hereby incorporated herein by reference.

Where the nucleic acid is an mRNA, it preferably encodes a polypeptide that is the gene product of one of the genes sequences of particular interest above. Where it is an antisense oligonucleotide, it may consist of ribonucleotides, and, optionally, a number of deoxynucleotides; e.g. it may function exclusively by binding to an mRNA, blocking transcription, or it may, in addition or alternatively, recruit RNAse H.

"dsRNA", as used herein, refers to a molecular species having a duplex structure comprising two anti-parallel and substantially complementary strands of nucleotides hybridized to each other. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop". Where the two strands are connected covalently by means other than an uninterrupted chain of nucleotides between the 3'-end of one strand and the 5'-end of the respective other strand forming the duplex structure, the connecting structure is referred to as a "linker". The RNA strands may have the same or a different number of nucleotides. The maximum number of base pairs is the number of nucleotides in the shortest strand of the dsRNA minus any overhangs that are present in the duplex. Where the two strands are connected by a hairpin loop, and the duplex structure consists of not more than 30 nucleotides, the dsRNA is referred to herein as an short hairpin RNA (shRNA). Where the two strands are not connected, or connected by a linker, and the duplex structure consists of not more than 30 nucleotides, the dsRNA is referred to herein as a short interfering RNA (siRNA).

An siRNA or shRNA generally includes one strand that is substantially complementary to at least part of an mRNA that occurs in the cell into which the siRNA or shRNA is to be introduced. Introducing an siRNA or shRNA into the cell then leads to degradation of the respective mRNA and thereby a perceived down-regulation of the corresponding gene.

Where the nucleic acid is a dsRNA, it preferably comprises at least 15, at least 18, at least 19, at least 20, at least 21, at least 22, at least 23, at least 25, at least 30, at least 50, at least 100, at least 200, at least 400, or at least 1000 base pairs, or it may consist of not more than 1000, not more than 400, not more than 200, not more than 100, not more than 50, not more than 30, not more than 25, not more than 23, not more than 22 or not more than 21 base pairs. "Consist of", in the context of the preceding sentence, is meant to limit exclusively the number of base pairs, not other structural features. For example, without limitation, the dsRNA may, in addition to a limited number of base pairs, e.g. not more than 30 base pairs, comprise single stranded regions, such as one or more of overhangs, bulges, loops, etc. It may also consist of only one double stranded region of consecutive nucleotide pairs, optionally with one or more single stranded overhangs. A single stranded overhang may generally reside on the 3'-end or the 5'-end of either strand, and it may consist of not more than 100, not more than 20, not more than 10, not more than 5, or not more than 4 nucleotides. Preferably, such overhang is 2 to 4 nucleotides in length, wherein overhangs of 2 nucleotides are preferred.

The introduction or transfer process of an anionic substance of interest into a cell is by itself well known. "Introduction or transfer" means that the anionic substance is, at the outset of the transfer process, located outside the cell or on the outer surface of the cell's membrane, and, at the end of the process, located inside said cell, or within its membrane, or on the inner surface of the membrane. If the anionic substance is a nucleic acid, "introduction or transfer" is also referred to as "transfection". Transfection can be verified by any appropriate method, for example by measuring the expression of a gene encoded by said nucleic acid, or by measuring the concentration of the expressed protein or its mRNA, or by measuring a biological, chemical or physical effect associated with its presence inside the cell.

"Capable of binding to" means that the considered compound is capable to interact and to bind to another compound, preferably in a reversible manner, for example by ionic interactions, by forming disulfide or hydrogen bonds, by hydrophobic interactions, e.g. van der Waals interactions, or covalent bonds. According to a particular embodiment, a peptide of the invention is capable of interacting and binding to an anionic substance of interest, preferably to a single stranded and/or double stranded nucleic acid. Preferably, a peptide of the invention is capable of interacting and binding to an anionic substance of interest at least by the intermediate of ionic interactions. Accordingly, the term "complex" refers to molecular assemblages of at least one peptide of the present invention and at least one anionic substance which are bound to one another via any one of the above described binding activities. Such a complex may contain further elements which are described below.

According to a particular embodiment, the complex of the invention further comprises: (iii) at least one ligand capable of cell-specific and/or nuclear targeting; and/or (iv) at least one further peptide capable of causing membrane disruption, and/or (v) at least one cationic compound selected from the group consisting of cationic lipids and cationic polymers, and/or (vi) a colipid.

The term "ligand capable of cell-specific targeting" refers to a ligand moiety which binds to a surface receptor of a cellular membrane (i.e. anti-ligand). Said cell membrane surface receptor is a molecule or structure which can bind said ligand with high affinity and preferably with high specificity. Said cell membrane surface receptor is preferably specific for a particular cell, i.e. it is found predominantly in one type of cell rather than in another type of cell (e.g. galactosyl residues to target the asialoglycoprotein receptor on the surface of hepatocytes). The cell membrane surface receptor facilitates cell targeting and internalization into the target cell of the ligand (i.e. the peptide involved in cell-specific targeting) and attached molecules (i.e. the complex of the invention).

A large number of ligand moieties/anti-ligands that may be used in the context of the present invention are widely described in the literature. Such a ligand moiety is capable of conferring to the complex of the invention, the ability to bind to a given anti-ligand molecule or a class of anti-ligand molecules localized at the surface of at least one target cell. Suitable anti-ligand molecules include without limitation polypeptides selected from the group consisting of cell-specific markers, tissue-specific markers, cellular receptors, viral antigens, antigenic epitopes and tumor-associated markers. Anti-ligand molecules may moreover consist of or comprise one or more sugar, lipid, glycolipid or antibody molecules. According to the invention, a ligand moiety may be for example a lipid, a glycolipid, a hormone, a sugar, a polymer (e.g. PEG, polylysine, PEI), an oligonucleotide, a vitamin, an antigen, all or part of a lectin, all or part of a polypeptide such as for example JTS1 (WO 94/40958), an antibody or a fragment thereof, or a combination thereof.

Preferably, the ligand moiety used in the present invention is a peptide or polypeptide having a minimal length of 7 amino acids. It is either a native polypeptide or a polypeptide derived from a native polypeptide. "Derived" means containing (a) one or more modifications with respect to the native sequence (e.g. addition, deletion and/or substitution of one or more residues), (b) amino acid analogs, including not naturally occurring amino acids or (c) substituted linkages or (d) other modifications known in the art. The polypeptides serving as ligand moiety encompass variant and chimeric polypeptides obtained by fusing sequences of various origins, such as for example a humanized antibody which combines the variable region of a mouse antibody and the constant region of a human immunoglobulin. In addition, such polypeptides may have a linear or cyclized structure (e.g. by flanking at both extremities a polypeptide ligand by cysteine residues). Additionally, the polypeptide in use as ligand moiety may include modifications of its original structure by way of substitution or addition of chemical moieties (e.g. glycosylation, alkylation, acetylation, amidation, phosphorylation, addition of sulfhydryl groups and the like). The invention further contemplates modifications that render the ligand moiety detectable. For this purpose, modifications with a detectable moiety can be envisaged (i.e. a scintigraphic, radioactive, or fluorescent moiety, or a dye label and the like). Suitable radioactive labels include but are not limited to $^{99}$Tc, $^{123}$I, and $^{111}$In. Such detectable labels may be attached to the ligand moiety by any conventional techniques and may be used for diagnostic purposes (e.g. imaging of tumoral cells).

In one special embodiment, the anti-ligand molecule is an antigen (e.g. a target cell-specific antigen, a disease-specific antigen, an antigen specifically expressed on the surface of engineered target cells) and the ligand moiety is an antibody, a fragment or a minimal recognition unit thereof (i.e. a fragment still presenting an antigenic specificity) such as those described in detail in immunology manuals (see for example Immunology, third edition 1993, Roitt, Brostoff and Male, ed Gambli, Mosby). The ligand moiety may be a monoclonal antibody. Monoclonal antibodies which will bind to many of these antigens are already known but in any case, with today's techniques in relation to monoclonal antibody technology, antibodies may be prepared to most antigens. The ligand moiety may be a part of an antibody (for example a Fab fragment) or a synthetic antibody fragment (for example, ScFv).

Suitable monoclonal antibodies to selected antigens may be prepared by known techniques, for example those disclosed in "Monoclonal Antibodies: A manual of techniques", H. Zola (CRC Press, 1988) and in "Monoclonal Hybridoma Antibodies: Techniques and Applications", J. G. R. Hurrell (CRC Press, 1982). Suitably prepared non-human antibodies may be "humanized" in known ways, for example by inserting the CDR regions of mouse antibodies into the framework of human antibodies. Additionally, as the variable heavy (VH) and variable light (VL) domains of the antibody are involved in antigen recognition, variable domains of rodent origin may be fused to constant domains of human origin such that the resultant antibody retains the antigenic specificity of the rodent parental antibody (Morrison et al (1984) Proc. Natl. Acad. Sci. USA 81, 6851-6855).

Antigenic specificity of antibodies is conferred by variable domains including Fab-like molecules (Better et al (1988) Science 240, 1041); Fv molecules (Skerra et al (1988) Science 240, 1038); ScFv molecules where the VH and VL partner domains are linked via a flexible oligopeptide (Bird et al (1988) Science 242, 423; Huston et al (1988) Proc. Natl. Acad. Sci. USA 85, 5879) and dAbs comprising isolated V domains (Ward et al (1989) Nature 341, 544). A general review of the techniques involved in the synthesis of antibody fragments which retain their specific binding sites is to be found in Winter & Milstein (1991) Nature 349, 293-299.

According to an advantageous embodiment, the ligand moiety is selected among antibody fragments, rather than whole antibodies. Effective functions of whole antibodies, such as complement binding, are removed. ScFv and dAb antibody fragments may be expressed as a fusion with one or more other polypeptides. Minimal recognition units may be derived from the sequence of one or more of the complementary-determining regions (CDR) of the Fv fragment. Whole antibodies, and F(ab')2 fragments are "bivalent". By "bivalent" we mean that said antibodies and F(ab') 2 fragments have two antigen binding sites. In contrast, Fab, Fv, ScFV, dAb fragments and minimal recognition units are monovalent, having only one antigen binding sites.

In a further embodiment the ligand moiety is at least part of a specific moiety implicated in natural cell-surface receptor binding. Of course, said natural receptors (e.g. hormone receptors) may also be target cell-specific antigens and may be recognized by ligand moieties which have the property of a monoclonal antibody, a ScFv, a dAb or a minimal recognition unit.

In a preferred embodiment, the ligand moiety allows to target a virally infected cell and is capable of recognizing and binding to a viral component (e.g. envelope glycoprotein) or capable of interfering with the virus biology (e.g. entry or replication). For example, the targeting of an HIV (Human Immunodeficiency Virus) infected cell can be performed with a ligand moiety specific for an epitope of the HIV envelope, such as a ligand moiety derived from the 2F5 antibody (Buchacher et al., 1992, Vaccines 92, 191-195) recognizing a highly conserved epitope of the transmembrane glycoprotein gp41 or with a ligand moiety interfering with HIV attachment to its cellular receptor CD4 (e.g. the extracellular domain of the CD4 molecule).

In another preferred embodiment, the ligand moiety allows to target a tumor cell and is capable of recognizing and binding to a molecule related to the tumor status, such as a tumor-specific antigen, a cellular protein differentially or over-expressed in tumor cells or a gene product of a cancer-associated virus.

Examples of tumor-specific antigens include but are not limited to MUC-1 related to breast cancer (Hareuveni et al., 1990, Eur. J. Biochem 189, 475-486), the products encoded by the mutated BRCA1 and BRCA2 genes related to breast and ovarian cancers (Miki et al., 1994, Science 226, 66-71; Futreal et al., 1994, Science 226, 120-122; Wooster et al., 1995, Nature 378, 789-792), APC related to colon cancer (Polakis, 1995, Curr. Opin. Genet. Dev. 5, 66-71), prostate specific antigen (PSA) related to prostate cancer, (Stamey et al., 1987, New England J. Med. 317, 909), carcinoma embryonic antigen (CEA) related to colon cancers (Schrewe et al., 1990, Mol. Cell. Biol. 10, 2738-2748), tyrosinase related to melanomas (Vile et al., 1993, Cancer Res. 53, 3860-3864), receptor for melanocyte-stimulating hormone (MSH) which is expressed in high number in melanoma cells, ErbB-2 related to breast and pancreas cancers (Harris et al., 1994, Gene Therapy 1, 170-175), and alpha-foetoprotein related to liver cancers (Kanai et al., 1997, Cancer Res. 57, 461-465).

A special ligand moiety in use in the present invention is a fragment of an antibody capable of recognizing and binding to the MUC-1 antigen and thus targeting the MUC-1 positive tumor cells. A more preferred ligand moiety is the scFv fragment of the SM3 monoclonal antibody which recognizes the tandem repeat region of the MUC-1 antigen (Burshell et al., 1987, Cancer Res. 47, 5476-5482; Girling et al., 1989, Int J. Cancer 43, 1072-1076; Dokurno et al., 1998, J. Mol. Biol. 284, 713-728).

Examples of cellular proteins differentially or overexpressed in tumor cells include but are not limited to the receptor for interleukin 2 (IL-2) overexpressed in some lymphoid tumors, GRP (Gastrin Release Peptide) overexpressed in lung carcinoma cells, pancreas, prostate and stomach tumors (Michael et al., 1995, Gene Therapy 2, 660-668), TNF (Tumor Necrosis Factor) receptor, epidermal growth factor receptors, Fas receptor, CD40 receptor, CD30 receptor, CD27 receptor, OX-40, α-v integrins (Brooks et al., 1994, Science 264, 569) and receptors for certain angiogenic growth factors (Hanahan, 1997, Science 277, 48). Based on these indications, it is within the scope of those skilled in the art to define an appropriate ligand moiety capable of recognizing and binding to such proteins. To illustrate, IL-2 is a suitable ligand moiety to bind to IL-2 receptor.

Suitable gene products of cancer-associated viruses include but are not limited to human papilloma virus (HPV) E6 and E7 early polypeptides as well as L1 and L2 late polypeptides (EP 0 462 187, U.S. Pat. No. 5,744,133 and WO98/04705) that are expressed in cervical cancer and EBNA-1 antigen of Epstein-Barr virus (EBV) associated with Burkitt's lymphomas (Evans et al., 1997, Gene Therapy 4, 264-267).

In still another embodiment, the ligand moiety allows to target tissue-specific molecules. For example, ligand moieties suitable for targeting liver cells include but are not limited to those derived from ApoB (apolipoprotein) capable of binding to the LDL receptor, alpha-2-macroglobulin capable of binding to the LPR receptor, alpha-1 acid glycoprotein capable of binding to the asialoglycoprotein receptor and transferrin capable of binding to the transferrin receptor. A ligand moiety for targeting activated endothelial cells may be derived from the sialyl-Lewis-X antigen (capable of binding to ELAM-1), from VLA-4 (capable of binding to the VCAM-1 receptor) or from LFA-1 (capable of binding to the ICAM-1 receptor). A ligand moiety derived from CD34 is useful to target hematopoetic progenitor cells through binding to the CD34 receptor. A ligand moiety derived from ICAM-1 is more intended to target lymphocytes through binding to the LFA-1 receptor. Finally, the targeting of T-helper cells may use a ligand moiety derived from HIV gp-120 or a class II MHC antigen capable of binding to the CD4 receptor.

By "target cells", we refer to the cells that the complex of the invention can selectively target. Depending on the nature of the ligand moiety and/or of the anti-ligand molecule, "target cells" may designate a unique type of cell or a group of different types of cells having as a common feature on their surface an anti-ligand molecule(s) recognized by ligand moiety(s) present in the complex of the invention. For the purpose of the invention, a target cell is any mammalian cell (preferably human cell) which can be targeted with a complex according to the present invention having a suitable ligand moiety. The term "to target" refers to addressing a certain type of cells or a group of types of cells for gene transfer in favour of the remaining part of the totality of cells being contacted with the complex of the present invention. The target cell may be a primary cell, a transformed cell or a tumor cell. Suitable target cells include but are not limited to hematopoetic cells (totipotent, stem cells, leukocytes, lymphocytes, monocytes, macrophages, APC, dendritic cells non-human cells and the like), muscle cells (satellite, myocytes, myoblasts, skeletal or smooth muscle cells, heart cells), pulmonary cells, tracheal cells, hepatic cells, epithelial cells, endothelial cells or fibroblasts.

The term "ligand capable of nuclear targeting" refers to a particular ligand which is capable of binding to a nuclear receptor (nuclear anti-ligand). Said nuclear receptor is a molecule or structure localized in or/and on the nuclear membrane which can bind to said ligand, thereby facilitating intracellular transport of the complex of the present invention towards the nucleus and its internalization into the nucleus. Examples of such a ligand involved in nuclear targeting are the nuclear signal sequences derived from the T-antigen of the SV40 virus (Lanford and Butel, 1984, Cell 37, 801-813) and from the EBNA-1 protein of the Epstein Barr virus (Ambinder et al., 1991, J. Virol. 65, 1466-1478).

In a special embodiment, the complex of the invention may comprise (iv) at least one further peptide capable of causing membrane disruption. Contrary to the peptide of the instant invention, said second peptide is not necessarily a peptide capable of binding with anionic molecules. Examples of such peptides are JTS-1, JTS-1-K13, GALA, KALA (see Mahato et al., 1999, Current Opinion in Mol. Therapeutics 1, 226-243; WO 96/40958; WO 98/50078; Gottschalk et al., 1996, Gene Therapy, 3, 448-457; Haensler & Szoka, 1993, Bioconjugate Chem., 4, 372-379; Wyman et al., 1997, Biochemistry, 36, 3008-3017).

In another embodiment, the complex of the invention may further comprise (v) at least one cationic compound selected from the group consisting of cationic lipids and cationic polymers. These cationic compounds are widely described in the scientific literature (see for example the references related to non-viral delivery systems mentioned above, or WO 97/29118, WO 98/08489, WO 98/17693). Cationic lipids or mixtures of cationic lipids which may be used in the present invention include cationic lipids selected from the group consisting of Lipofectin™, DOTMA: N-[1-(2,3-dioleyloxyl)propyl]-N,N,N-trimethylammon-ium (Felgner, PNAS 84 (1987), 7413-7417), DOGS: dioctadecylamidoglycylspermine or Transfectam™ (Behr, PNAS 86 (1989), 6982-6986), DMRIE: 1,2-dimiristyloxypropyl-3-dimethyl-hydroxyethylammonium and DORIE: 1,2-diooleyloxypropyl-3-dimethyl-hydroxyethylammnoium (Felgner, Methods 5 (1993), 67-75), DC-CHOL: 3 [N-(N',N'-dimethylaminoethane)-carbamoyl]cholesterol (Gao, BBRC 179 (1991), 280-285), DOTAP (McLachlan, Gene Therapy 2 (1995), 674-622), Lipofectamine™, spermine or spermidine-cholesterol, Lipofectace™ (for a review see for example Legendre, Medecine/Science 12 (1996), 1334-1341 or Gao, Gene Therapy 2 (1995), 710-722), cationic lipid as disclosed in patent applications WO 98/34910, WO 98/14439, WO 97/19675, WO 97/37966 and their isomers. Nevertheless, this list is not exhaustive and other cationic lipids well known in the art can be used in connection with the present invention as well.

Preferably, the cationic lipids of the present invention are selected from the cationic lipids having the formula (EP 901 463):

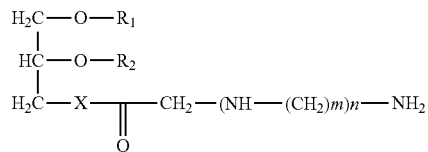

wherein:

$R_1$, $R_2$, are identical or different and are $C_6$-$C_{23}$ alkyl or alkenyl groups, linear or branched, or —C(O)—($C_6$-$C_{23}$) alkyl or —C(O)—($C_6$-$C_{23}$) alkenyl, linear or branched, X is O or —$NR_3$, $R_3$ being H or $C_1$-$C_4$ alkyl, n=1 to 6, m=1 to 6, and when n>1, m can be identical or different in each n repeat.

Cationic polymers or mixtures of cationic polymers which may be used in the present invention include cationic polymers selected from the group consisting of chitosan, poly (aminoacids) such as polylysine (U.S. Pat. No. 5,595,897 and FR 2 719 316); polyquaternary compounds; protamine; polyimines; polyethylene imine or polypropylene imine (WO 96/02655); polyvinylamines; polycationic polymer derivatized with DEAE, such as pullulans, celluloses; polyvinylpyridine; polymethacrylates; polyacrylates; polyoxethanes; polythiodiethylaminomethylethylene (P(TDAE)); polyhistidine; polyornithine; poly-p-aminostyrene; polyoxethanes; co-polymethacrylates (eg copolymer of HPMA; N-(2-hydroxypropyl)-methacrylamide); the compound disclosed in U.S. Pat. No. 3,910,862, polyvinylpyrrolid complexes of DEAE with methacrylate, dextran, acrylamide, polyimines, albumin, dimethylaminomethylmethacrylates and polyvinylpyrrolidonemethylacryl-aminopropyltrimethyl ammonium chlorides; polyamidoamines; telomeric compounds. Nevertheless, this list is not exhaustive and other cationic polymers well known in the art can be used in connection with the present invention as well.

Colipids (vi) may be optionally included in the complex of the invention in order to facilitate entry of the nucleic acid into the cell. According to the invention, colipids are selected from the group consisting of positively or negatively charged, neutral or zwitterionic lipids. These colipids are, for example, selected from the group consisting of phosphatidylethanolamine (PE), phosphatidylcholine, phosphocholine, dioleylphosphatidylethanolamine (DOPE), sphingomyelin, ceramide or cerebroside and one of their derivatives.

The various elements of the complex (i.e. ligand, peptide, anionic or cationic compounds) may be modified or substituted by chemical or natural processes widely used by the skilled man in order to obtain compounds modified or substituted such as those disclosed above, enabling, for example, visualization of the distribution of the polypeptide expressed by the nucleic acid, of the nucleic acid, or of the complex of the invention, after in vitro or in vivo administration of the complex.

In a specific embodiment of the invention, the size of the complex according to the invention is small (i.e. its diameter is less than 2 μm, preferably less than 500 nm and, most preferably, it ranges between 20 and 100 nm). The size of the complex may be selected for optimal use in particular applications. Measurements of the complex size can be achieved by a number of techniques including, but not limited to, dynamic laser light scattering (photon correlation spectroscopy, PCS), as well as other techniques known to those skilled in the art (see, Washington, Particle Size Analysis in Pharmaceutics and other Industries, Ellis Horwood, New York, 1992, 135-169). Sizing procedure may also be applied on complexes in order to select specific complex sizes. Methods which can be used in this sizing step include, but are not limited to, extrusion, sonication and microfluidization, size exclusion chromatography, field flow fractionation, electrophoresis and ultracentrifugation.

Preferably, the molar ratio (peptide):(nucleic acid) in the complex is between 1:100 and 100:1, more preferably between 1:1 and 20:1, yet more preferably between 5:1 and 15:1, most preferably between 8:1 and 13:1, and specifically 8:1, 10:1, or 12:1. The optimal molar ratio is easily determined by the skilled person, for example as described herein below. Specifically, the skilled person can test the transfection efficiency of complexes having a variety of molar ratios (peptide):(nucleic acid) for any given peptide/nucleic acid combination, and will chose the ratio giving the best transfection efficiency.

As a preferred embodiment of the invention, the ratio between the number of positive charges and the number of negative charges of the complex is between 0.05 and 20, preferably said ratio is up to 1. The complex of the invention may be characterized by its theoretical charge ratio (+/−), which is the ratio of the positive charges provided by at least the peptide of the invention (i) to the negative charges provided by at least the anionic substance of interest (ii) in the complex, assuming that all potentially cationic groups are in fact in the cationic state and all potentially anionic groups are in fact in the anionic state. In general, an excess of positive charges on the complex facilitates binding of the complex to the negatively-charged cell surface. To obtain such a ratio, the calculation shall take into account all negative charges in the anionic substance and shall then adjust the quantity of the peptide of the present invention necessary to obtain the desired theoretical charge ratio as defined above. The quantities and the concentrations of the other ingredients (i)-(vi), if any, shall be taken into account in function of their respective molar masses and their number of positive and negative charges. The ratio is not specifically limited. As a preferred embodiment the above identified quantities are selected so that the ratio between the number of positive charges and the number of negative charges is between 0.05 and 20, preferably said charge ratio is up to 1.

The ratio of cationic lipids and/or cationic polymers to colipid (on a weight to weight basis), when the compounds are co-existing in the complex, can range from 1:0 to 1:10. In preferred embodiments, this ratio ranges from 1:0.5 to 1:4.

The compound and charge ratios indicated herein are not meant to be limiting as one skilled in the art could readily practice the teachings of the invention using any ratio of the herein disclosed components.

Furthermore, the concentration of the anionic substance of interest (ii) which may be added to the peptide to form said complex of the invention may range from 1 μg/ml to 5000 μg/ml. In a preferred embodiment of the invention, the concentration of said anionic substance of interest ranges from 100 μg/ml to 1000 μg/ml. Doses based on a plasmid or synthetic vector may comprise between 0.01 and 100 mg of DNA, advantageously between 0.05 and 10 mg and preferably between 0.5 and 5 mg.

The invention is also directed to a method for manufacturing the above described composition, comprising the following steps:

contacting at least one peptide of the present invention with an anionic substance of interest, and recovering said complex, optionally after a purification or selection step.

Where the complex of the invention further comprises:

(iii) at least one ligand capable of cell-specific and/or nuclear targeting; and/or (iv) at least one further peptide which is capable of causing membrane disruption; and/or (v) at least one cationic compound selected from the group consisting of cationic lipids and cationic polymers; and/or (vi) at least one colipid.

said process comprises the steps of:

first mixing said peptide (i) with said additional element (iii) and/or (iv) and/or (v) and/or (vi) and then complexing the anionic substances of interest, or first complexing said peptide (i) with the anionic substances of interest (ii) and then mixing the complex with said additional element (iii) and/or (iv) and/or (v) and/or (vi).

The process can further comprise a sizing procedure as described above.

The invention also encompasses a composition, preferably for transferring an anionic substance of interest into a cell, wherein said composition comprises at least one complex as previously disclosed.

This composition can be formulated in various forms, e.g. in solid, liquid, powder, aqueous, or lyophilized form.

In a preferred embodiment, this composition further comprises a pharmaceutically acceptable carrier, allowing its use in a method for the therapeutic treatment of humans or animals. Such compositions are herein referred to as pharmaceutical compositions of the invention. In this particular case, the carrier is preferably a pharmaceutically suitable injectable carrier or diluent (for examples, see Remington's Pharmaceutical Sciences, 16.sup.th ed. 1980, Mack Publishing Co). Such a carrier or diluent is pharmaceutically acceptable, i.e. is non-toxic to a recipient at the dosage and concentration employed. It is preferably isotonic, hypotonic or weakly hypertonic and has a relatively low ionic strength, such as provided by a sucrose solution. Furthermore, it may contain any relevant solvents, aqueous or partly aqueous liquid carriers comprising sterile, pyrogen-free water, dispersion media, coatings, and equivalents, or diluents (e.g. Tris-HCl, acetate, phosphate), emulsifiers, solubilizers or adjuvants. The pH of the pharmaceutical preparation is suitably adjusted and buffered in order to be useful in in vivo applications. It may be prepared either as a liquid solution or in a solid form (e.g. lyophilized) which can be suspended in a solution prior to administration. Representative examples of carriers or diluents for an injectable composition include water, isotonic saline solutions which are preferably buffered at a physiological pH (such as phosphate buffered saline or Tris buffered saline), mannitol, dextrose, glycerol and ethanol, as well as polypeptides or proteins such as human serum albumin. For example, such composition comprise 10 mg/ml mannitol, 1 mg/ml HSA, 20 mM Tris pH 7.2 and 150 mM NaCl.

Said composition is particularly useful for the delivery of polynucleotides to cells or tissues of a subject, e.g. in connection with gene therapy methods, but are not limited to such uses. The term "gene therapy method" is preferably understood as a method for the introduction of a polynucleotide into cells either in vivo or by introduction into cells in vitro followed by re-implantation into a subject. "Gene therapy" in particular concerns the case where the gene product is expressed in a tissue as well as the case where the gene product is excreted, especially into the blood stream. In such embodiments, the product of the gene to be introduced will be beneficial to the patient, and is underrepresented or underexpressed in cells of the patient.

However, in the case of diseases, disorders or conditions, where an undesirable gene product is present in the patient, or a gene is overexpressed in the patient, the pharmaceutical composition of the invention intended for the treatment of such patient will usually comprise an antisense oligonucleotide, ribozyme, or dsRNA mediating RNA interference, which is specific for the gene encoding the undesirable gene product or overexpressed gene, i.e. the target gene for a treatment. That is, the antisense oligonucleotide, ribozyme, or dsRNA mediating RNA interference will comprise a sequence that is substantially complementary to the target gene, or a structure able to specifically cleave an mRNA expressed from the target gene.

The invention more particularly relates to a composition comprising at least one of the complexes described above and at least one adjuvant capable of improving the transfection capacity of said complex. Adjuvants may be selected from the group consisting of a chloroquine, protic polar compounds, such as propylene glycol, polyethylene glycol, glycerol, EtOH, 1-methyl L-2-pyrrolidone or their derivatives, or aprotic polar compounds such as dimethylsulfoxide (DMSO), diethylsulfoxide, di-n-propylsulfoxide, dimethylsulfone, sulfolane, dimethylformamide, dimethylacetamide, tetramethylurea, acetonitrile or their derivatives.

In another aspect, the invention encompasses a method to treat a subject, comprising the step of: administering to the subject a pharmaceutical composition of the invention. A pharmaceutical composition of the present invention can be administered into a vertebrate. This administration may be carried out by an intradermal, subdermal, intravenous, intramuscular, intranasal, intracerebral, intratracheal, intraarterial, intraperitoneal, intravesical, intrapleural, intracoronary or intratumoral injection, by means of a syringe or other devices. Transdermal administration is also contemplated, such as inhalation, aerosol routes, instillation or topical application. "Vertebrate" as used herein is intended to have the same meaning as commonly understood by one of ordinary skill in the art. Particularly, "vertebrate" encompasses mammals, and more particularly humans.

According to the present invention, the pharmaceutical composition can be administered into tissues of the vertebrate body including those of muscle, skin, brain, lung, liver, spleen, bone marrow, thymus, heart, lymph, bone, cartilage, pancreas, kidney, gall bladder, stomach, intestine, testis, ovary, uterus, rectum, nervous system, eye, gland, connective tissue, blood, tumor, etc.

Applied to in vivo therapy, this invention allows repeated administration to the patient without any risk of the administered preparation to induce a significant immune reaction. Administration may be by single or repeated dose, once or several times after a certain period of time. Repeated administration allows a reduction of the dose of active substance, in particular nucleic acid, administered at a single time. The route of administration and the appropriate dose varies depending on several parameters, for example the individual patient, the disease being treated, or the nucleic acid being transferred. The invention can be applied in vivo to the interstitial or luminal space of tissues in the lungs, the trachea, the skin, the muscles, the brain, the liver, the heart, the spleen, the bone marrow, the thymus, the bladder, the lymphatic system, the blood, the pancreas, the stomach, the kidneys, the ovaries, the testicles, the rectum, the peripheral or central nervous system, the eyes, the lymphoid organs, the cartilage, or the endothelium. In the case of in vivo treatment according to the invention, in order to improve the transfection rate, the patient may undergo a macrophage depletion treatment prior to administration of the pharmaceutical preparation as described above. Such a technique is described in the literature (refer particularly to Van Rooijen et al., 1997, TibTech, 15, 178-184).

The present invention also encompasses a method to introduce an anionic substance into a cell is provided, comprising the steps of: (1) contacting the anionic substance with a peptide of the invention, such that a complex is formed, and (2) contacting said cell with said complex. This process may be applied by direct administration of said complex to cells of a vertebrate in vivo, or by in vitro treatment of cells which were recovered from the vertebrate and then re-introduced into the vertebrate body (ex vivo process). In in vitro applications, cells cultivated on an appropriate medium are placed in contact with a suspension containing a complex or composition of the invention. After an incubation time, the cells are washed and recovered. Introduction of the active substance can be verified (eventually after lysis of the cells) by any appropriate method.

Finally, the present invention also provides the use of a peptide according to the invention for the preparation of a pharmaceutical composition for curative, preventive or vaccine treatment of mammals. Preferably, such compositions are intended for the treatment of the human or animal body. "Treatment" as used herein refers to prophylaxis and therapy. It concerns both the treatment of humans and animals. A "therapeutically effective amount of a peptide or a composition" is a dose sufficient for the alleviation of one or more symptoms normally associated with the disease desired to be treated. A method according to the invention is preferentially intended for the treatment of the diseases listed above.

The invention further concerns a cell comprising a peptide of the invention, optionally in a complex with an anionic substance. Preferred embodiments of the instant cell are as provided for other inventive aspects above. According to the invention, "cells" include prokaryotic cells and eukaryotic cells, yeast cells, plant cells, human or animal cells, in particular mammalian cells. In particular, cancer cells should be mentioned. In preferred embodiments, the cell will be a muscle cell, as stem cell of the hematopoietic system or an airways cell, more especially a tracheal or pulmonary cell, and preferably a cell of the respiratory epithelium.

These and other embodiments are disclosed or are obvious from and encompassed by the description and examples of the present invention. Further literature concerning any one of the methods, uses and compounds to be employed in accordance with the present invention may be retrieved from public libraries, using for example electronic devices. For example the public database "Medline" may be utilized which is available on Internet, e.g. under http://www.ncbi.nlm.nih.gov/PubMed/medline.html. Further databases and addresses, such as http://www.ncbi.nlm.nih.gov, http://www.infobiogen.fr, http://www.fmi.ch/biology/research$_1$3 tools.html, http://www.tigr.org, are known to the person skilled in the art and can also be obtained using, e.g., http://www.lycos.com. An overview of patent information in biotechnology and a survey of relevant sources of patent information useful for retrospective searching and for current awareness is given in Berks, TIBTECH 12 (1994), 352-364.

The methods, compositions and uses of the invention can be applied in the treatment of all kinds of diseases the treatment and/or diagnostic of which is related to or dependent on the transfer of nucleic acids in cells. The compositions, and uses of the present invention may be desirably employed in humans, although animal treatment is also encompassed by the uses described herein.

The invention has been described in an illustrative manner, and it is to be understood that the terminology which has been used is intended to be in the nature of words of description rather than of limitation. Obviously, many modifications and variations of the present invention are possible in light of the above teachings. It is therefore to be understood that within the scope of the appended claims, the invention may be practiced different from what is specifically described herein.

The disclosure of all patents, publications, published patent applications, and database entries cited in the present application are hereby incorporated by reference in their entirety to the same extent as if each such individual patent, publication and database entry were specifically and individually indicated to be incorporated by reference and were set forth in its entirety herein.

EXAMPLES

1. Materials

Where the source of a reagent is not specifically given herein, such reagent may be obtained from any supplier of reagents for molecular biology at a quality/purity standard for application in molecular biology.

All peptides employed herein were obtained as custom synthesis from Thermo Electron GmbH, Ulm, Germany, at a purity exceeding 97%. Custom synthesis followed routine procedures in solid phase peptide synthesis, such as those described in Atherton, E., Sheppard, R. C., Solid Phase peptide synthesis: a practical approach, IRL Press, Oxford, England, 1989, or Stewart J. M., Young, J. D., Solid phase peptide synthesis, 2nd edition, Pierce Chemical Company, Rockford, 1984.

Single-stranded RNAs were produced by solid phase synthesis on a scale of 1 μmole using an Expedite 8909 synthesizer (Applied Biosystems, Applera Deutschland GmbH, Darmstadt, Germany) and controlled pore glass (CPG, 500 Å, Proligo Biochemie GmbH, Hamburg, Germany) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification of the crude oligoribonucleotides by anion exchange HPLC were carried out according to established procedures. Yields and concentrations were determined by UV absorption of a solution of the respective RNA at a wavelength of 260 nm using a spectral photometer (DU 640B, Beckman Coulter GmbH, Unterschleißheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The annealed RNA solution was diluted to a concentration of 50 μmole double stranded RNA/I and stored at −20° C. until use.

2. Identifying a Suitable Cell Penetrating Petide

We investigated several known cell penetrating peptides (CPP) (summarized in Table 1) for their ability to deliver siRNAs functionally to various cell lines. Instead of using fluorescently labelled siRNAs to evaluate cellular uptake, we measured the modulation of the target mRNA. This addresses not only the total cellular uptake but also the issue of delivery to the right intracellular compartment for RNA interference activity.

TABLE 1

Cell penetrating peptides tested for siRNA delivery

| Name | Amino acid sequence[1] | Molar ratio peptide/ siRNA | SEQ ID NO: |
|---|---|---|---|
| Penetratin (pAntp) | RQIKIWFQNRRMKWKK | 7.5:1 | 9 |

TABLE 1-continued

Cell penetrating peptides tested for siRNA delivery

| Name | Amino acid sequence[1] | Molar ratio peptide/ siRNA | SEQ ID NO: |
|---|---|---|---|
| Penetratin-Cystein | RQIKIWFQNRRMKWKKC | 10:1 | 10 |
| Transportan 10 | AGYLLGKINLKALAALAKKIL-amide | 12.5:1 | 11 |
| MPG peptide | GALFLGWLGAAGSTMGAPKKKRKV-amide | 17.5:1 | 12 |
| ppTG1 | GLFKALLKLLKSLWKLLLKA | 12.5:1 | 13 |
| ppTG20 | GLFRALLRLLRSLWRLLLRA | 8:1 | 14 |
| Cys-ppTG20 | CGLFRALLRLLRSLWRLLLRA | 10:1 | 15 |
| Argenine | RRRRRRRR | 10:1 | 16 |
| NM574 | YARVRRRGPRR | 7:1 | 17 |

[1]All peptides are C-terminal free acid unless stated otherwise

Delivery of siRNAs was tested in 7 different cell lines we obtained from the American Type Culture Collection, ATCC, via LCG Promochem GmbH, Wesel, Germany (PC12, ATTC# CRL-1721; HCT116, ATCC# CCL-247; C33A, ATCC# HTB-31; H441, ATCC# HTB-174; NMuLi, ATCC# CRL-1638; HepG2, ATCC# HB-8065; HeLa S3, ATCC# CCL2.2) and in the cell line KB-BCL2-GFP, as described in co-pending U.S. Ser. No. 10/941,663. Target mRNA quantification was performed using the QuantiGene™ bDNA-kit from Panomics, Inc., Fremont, USA, according to the manufacturers instructions, and essentially as described below for H441 cells. Genes constitutively expressed in the various cell lines were chosen as targets and results normalized to GAPDH expression. siRNA concentration was 250 nM, the concentration of the peptide was chosen as given by the molar ratio peptide/siRNA shown in Table 1. Cytotoxicity of peptides was evaluated employing the CytoTox-ONE™ assay (Promega GmbH, Mannheim, Germany).

By this approach we identified ppTG20 as effective in delivering siRNAs to all 8 cell lines tested. Closer inspection of the intracellular localization by fluorescence microscopy using a Cy3-labelled siRNA complexed with ppTG20 revealed a strong signal in the perinuclear region.

3. Determination of Optimal (Peptide):(Anionic Substance) Ratio

To determine the optimal ratio of (peptide):(anionic substance) for complex formation, a fixed concentration of the anionic substance was titrated with increasing amounts of the peptide, and complex formation was monitored. E.g., where the peptide is cationic, the concentration at which the positive charges on the peptide cancel the negative charges on the anionic substance may be monitored by electrophoresis of the mixture.

To this end, 20 µmolar solutions of dsRNA AL-DP-5107, nucleic acid sequences: sense strand 5'-ccacaugaagcagcac-gacuu-3' (SEQ ID NO: 18); antisense strand 5'-aagucgugcugcuucaugugg$_{2'-OMe}$su$_{2'-OMe}$sc-3' (SEQ ID NO: 19; lower case a, g, u, c: ribonucleotides; s: phosphorothioate backbone linkage; Subscript 2'-OMe: 2'-O-methyl ribonucleotide), were incubated with equal volumes of aequeous solutions containing, e.g., 1000, 500, 250, 150, 80, 40 or 20 µmole/l of ppTG20 or ppTGHis for 30 min at room temperature, and then kept at 4° C. until analysis.

Analysis was performed by PAGE electrophoresis on a 10% acrylamide gel (for 4 gels: mix 15 ml 40% aequeous acrylamide (Rotiphorese Gel 40 (19:1), Carl Roth GmbH & Co KG, Karlsruhe, Germany, Cat.-No. 3030.1) solution with 6 ml 10XTBE (Tris Borate EDTA), 39 ml deionized water, 180 µl 10% (wt/vol) aequeous ammonium peroxosulfate and 90 µl TEMED solution) in a Hoefer miniVE electrophoresis unit (Hoefer, Inc., San Francisco, USA) using 0.8XTBE as running buffer. The gel was pre-run at 80V for 20 min before applying samples. 10 µl of the solution containing the siRNA/peptide complexes were mixed with 10 µl gel loading buffer (65% (wt/vol) Sucrose, 10 mmolar Tris-HCl (pH 7.5), 10 mmolar EDTA 0,3% (wt/vol) Xylencyanol) and loaded onto the gel. Gels were run for 1.25 h at 100V, removed from the apparatus, and stained for 30 min in Stains-all (Sigma Aldrich GmbH, Taufkirchen, Germany, Cat.-No. E7762; 50 mg Stains-all dissolved in 1 l of 50% (vol/vol) aequeous formamide). Excess Stains-all was removed by steeping the gel in water for another 30 min.

SiRNA was detectable, in the above example, starting at a ratio of 75 µmolar peptide/10 µmolar siRNA. Hence, the lowest molar ratio of peptide/siRNA that still yields complete complexation of the siRNA is expected to fall in the range of 8:1 to approximately 13:1. A ratio of 12.5:1 was used for further experiments in H441 cells.

4. Single Dose Screen in H441 Cells of ppTG20 and a Modified CPP, ppTGHis

In order to test the potential of adding Histidine residues for improving the cross-membrane transport properties of peptides, we synthesized a modified ppTG20, termed ppTGHis herein, wherein 4 consecutive Histidine moieties were added to the C-terminus of ppTG20. We then compared the transport of siRNAs complexed with ppTG20 or ppTGHis into H441 cells, as evaluated by the ability of siRNAs to inhibit the expression of a gene constitutively expressed in H441 cells, ENaC-alpha.

4.1. Cell Culture

H441 cells (American Type Culture Collection (ATCC) Cat. No. HTB-174, obtained from LCG Promochem GmbH, Wesel, Germany) were grown in the following medium: RPMI 1640, 10% fetal calf serum, 100 u/ml penicillin, 100 µg/ml streptomycin, 2 mmolar L-glutamine, 10 nmolar Hepes and 1 mmolar Sodium-Pyruvate (all from Biochrom AG, Berlin, Germany).

4.2. Transfection and mRNA Quantification

One day before transfection, ENaC-alpha expression was induced in H441 cells by adding dexamethasone to the growth medium to a final concentration of 100 nmolar.

H441 cells were transfected with siRNA/Lipofectamine™, siRNA/ppTG20, or siRNA/ppTGHis. The antisense strand of the siRNA we used, denominated AD-7007, (nucleic acid sequences: sense strand 5'-gucucccucugucacgaugTT-3', SEQ ID NO: 20; antisense strand 5'-caucgugacagagggagacTT-3', SEQ ID NO: 21; lower case letters: ribonucleotides; capital letters: deoxyribonucleotides) is complementary to a partial sequence in the human mRNA for the gene ENaC-alpha, and has been shown to efficiently inhibit the expression of human ENaC-alpha upon transfection, e.g. using lipofectamine, in H441 cells (data not shown).

For transfection with peptide/siRNA complexes, H441 cells were seeded at $1.5 \times 10^4$ cells/well on 96-well plates (Greiner Bio-One GmbH, Frickenhausen, Germany) in 75 µl of growth medium. Transfection of cells was carried out with siRNA/lipofectamine 2000 (Invitrogen GmbH, Karlsruhe, Germany, cat. No. 11668-019) as described by the manufacturer, or with siRNAs preincubated with the inventive peptides as described above. Cells were transfected for 24 h at 37° C. and 5% $CO_2$ in a humidified incubator (Heraeus GmbH, Hanau). Thereafter, the cells were lysed by adding 50 μl of lysis mixture (content of the QuantiGene bDNA-kit from Panomics, Inc., Fremont, USA) to each well containing 100 μl of growth medium at 53° C. for 30 min, and ENaC mRNA levels were subsequently quantified with the Quantigene Explore Kit (Panomics, Inc., Dumbarton Circle Fremont, USA, cat. No. QG-000-02) according to the manufacturer's protocol. Finally, chemoluminescence was measured in a Victor2-Light (Perkin Elmer, Wiesbaden, Germany) as RLUs (relative light units) and values obtained with the hENaC probeset were normalized to the respective GAPDH values for each well (probe sequences shown in Table 2 and Table 3). Readings were obtained in quadruplicates for each transfection mix. Mock transfected cells (i.e. medium only used in transfection procedure) were used as control. The activity of a given siRNA/transfectant complex was expressed as percent ENaC mRNA concentration in treated cells relative to ENaC mRNA concentration in mock transfected cells.

TABLE 2 bDNA probe set used in determination of human ENaC-alpha mRNA content in cells

| FPL Name | Function | Sequence | SEQ ID No: |
|---|---|---|---|
| hENAC001 | CE | GTCTGTCCAGGGTTTCCTTCCTTTTTCTCTTGGAAAGAAAGT | 22 |
| hENAC002 | CE | ACTGCCATTCTTGGTGCAGTTTTTTCTCTTGGAAAGAAAGT | 23 |
| hENAC003 | CE | CTCTCCTGGAAGCAGGAGTGAATATTTTTCTCTTGGAAAGAAAGT | 24 |
| hENAC004 | CE | GCCGCGGATAGAAGATGTAGGTTTTTCTCTTGGAAAGAAAGT | 25 |
| hENAC005 | CE | GCACTTGGTGAAACAGCCCAGTTTTTCTCTTGGAAAGAAAGT | 26 |
| hENAC006 | CE | AGCAGAGAGCTGGTAGCTGGTCTTTTTCTCTTGGAAAGAAAGT | 27 |
| hENAC007 | LE | CGCCATAATCGCCCCCAATTTTTAGGCATAGGACCCGTGTCT | 28 |
| hENAC008 | LE | CACAGCCACACTCCTTGATCATGTTTTTAGGCATAGGACCCGTGTCT | 29 |
| hENAC009 | LE | ACAGTACTCCACGTTCTGGGTTTTTAGGCATAGGACCCGTGTCT | 30 |
| hENAC010 | LE | GGAGCTTATAGTAGCAGTACCCCTTTTTAGGCATAGGACCCGTGTCT | 31 |
| hENAC011 | LE | ACGCTGCATGGCTTCCGTTTTTAGGCATAGGACCCGTGTCT | 32 |
| hENAC012 | LE | GAGGGCCATCGTGAGTAACCTTTTTAGGCATAGGACCCGTGTCT | 33 |
| hENAC013 | BL | TCATGCTGATGGAGGTCTCCA | 34 |
| hENAC014 | BL | GGTAAAGGTTCTCAACAGGAACATC | 35 |
| hENAC015 | BL | CACACCTGCTGTGTGTACTTTGAAG | 36 |
| hENAC016 | BL | CAGGAACTGTGCTTTCTGTAGTC | 37 |
| hENAC017 | BL | GTGGTCTGAGGAGAAGTCAACCT | 38 |
| hENAC018 | BL | CCATTCCTGGGATGTCACC | 39 |

TABLE 3 bDNA probe set used in determination of human GAPDH mRNA content in cells

| FPL Name | Function | Sequence | SEQ ID NO: |
|---|---|---|---|
| hGAP001 | CE | GAATTTGCCATGGGTGGAATTTTTCTCTTGGAAAGAAAGT | 40 |
| hGAP002 | CE | GGAGGGATCTCGCTCCTGGATTTTTCTCTTGGAAAGAAAGT | 41 |
| hGAP003 | CE | CCCCAGCCTTCTCCATGGTTTTTCTCTTGGAAAGAAAGT | 42 |

TABLE 3-continued bDNA probe set used in determination of human GAPDH mRNA content in cells

| FPL Name | Function | Sequence | SEQ ID NO: |
|---|---|---|---|
| hGAP004 | CE | GCTCCCCCCTGCAAATGAGTTTTTCTCTTGGAAAGAAAGT | 43 |
| hGAP005 | LE | AGCCTTGACGGTGCCATGTTTTTAGGCATAGGACCCGTGTCT | 44 |
| hGAP006 | LE | GATGACAAGCTTCCCGTTCTCTTTTTAGGCATAGGACCCGTGTCT | 45 |
| hGAP007 | LE | AGATGGTGATGGGATTTCCATTTTTTTAGGCATAGGACCCGTGTCT | 46 |
| hGAP008 | LE | GCATCGCCCCACTTGATTTTTTTTAGGCATAGGACCCGTGTCT | 47 |
| hGAP009 | LE | CACGACGTACTCAGCGCCATTTTTAGGCATAGGACCCGTGTCT | 48 |
| hGAP010 | LE | GGCAGAGATGATGACCCTTTTGTTTTTAGGCATAGGACCCGTGTCT | 49 |
| hGAP011 | BL | GGTGAAGACGCCAGTGGACTC | 50 |

4.3. Results

Results are presented in Table 4. They show that the transfection efficiency and resulting siRNA activity of ppTGHis is comparable to that of Lipofectamine™, and approximately 10-fold better than ppTG20.

TABLE 4

Remaining ENaC mRNA concentration in % of mock transfected controls in H441 cells transfected with AD-7007/Lipofectamine ™ or various concentrations of AD-7007/ppTG20 or AD-7007/ppTGHis

| Transfection conditions | Remaining ENaC mRNA concentration in % of mock transfected controls (errors are Std. devs. of quadruplicate determinations |
|---|---|
| Mock transfection | 100% ± 22% |
| 50 nM AD-7007 + Lipofectamine | 9% ± 3% |
| 250 nM AD-7007 + 3.13 µM ppTGHis | 11% ± 2% |
| 25 nM AD-7007 + 313 nM ppTGHis | 31% ± 7% |
| 250 nM AD-7007 + 3.13 µM ppTG20 | 24% ± 6% |
| 25 nM AD-7007 + 313 nM ppTG20 | 85% ± 35% |

5. Introduction of siRNAs-CPP Complexes into HCT116-cells and Determination of E6AP Gene Expression Inhibition by bDNA Assay All further experiments were carried out using HCT116 cells and inhibition of E6AP expression as readout.

5.1. Cell Culture

HCT116-cells were obtained from the American Type Culture Collection (ATCC# CCL-247). They were cultured in McCoy's 5A medium (Biochrom AG, Berlin, Germany, Cat.# F1015) containing 10% fetal calf serum (FCS; Biochrom AG, Berlin, Germany, Cat.# S0115) and 2 mM L-Glutamin (Biochrom AG, Berlin, Germany, Cat.#: K0283) (standard growth medium). For incubation with peptide/siRNA, complexes, the medium was replaced by serum-free McCoy's 5A medium containing 2 mM L-Glutamin (serum free medium). After incubation with complexes for 4 h, McCoy's 5A medium containing 30% fetal calf serum and 2 mM L-Glutamin (triple FCS medium) was added to restore an overall 10% FCS in the medium.

5.2. siRNA/peptide Complexes

The E6AP-specific siRNA denoted AD-8724 herein was used, having the following sequences: antisense strand: 5'-ucacauuccacguuaggugTsT-3' (SEQ ID NO:51), sense strand 5'-caccuaacguggaaugugaTsT-3'; (SEQ ID NO:52; lower case letters: ribonucleotides; s: phosphorothioate backbone linkage). As a negative control, an siRNA specific for eGFP, denoted AD-5107 herein, was used, having the following sequences: antisense strand: 5'-aagucgugcugcuucaugug-g$_{OMe}$su$_{OMe}$sc-3' (SEQ ID NO:19), sense strand 5'-ccacaugaagcagcacgacuu-3' (SEQ ID NO:18; lower case letters: ribonucleotides; subscript OMe: 2'-O-methyl-ribonucleotide; s: phosphorothioate backbone linkage). In addition to the non-specific control siRNA AD-5107, mock transfected cells treated with standard growth medium only were used as negative controls. As a positive control, AD-8724 was transfected into the cells using Lipofectamine2000™ (Invitrogen, Karlsruhe, Germany, Cat. No. 11668-019). As a further control, AD-5107 was transfected into cells using Lipofectamine2000™. All assays were performed in quadruplicates.

SiRNA/peptide complexes were prepared by mixing a solution of the siRNA in deionized water with a solution of the peptide in deionized water at the appropriate concentrations to give the desired ratio of siRNA/peptide at the desired concentration of the complex. The mixture was incubated at room temperature for 30 min and kept at 4° C. until use, and used within 24 h.

5.3. Transfection Protocol

For transfections with siRNA/peptide complexes, 1.5×10$^5$ HCT116-cells per well in 150 µl standard growth medium were seeded into polystyrene 96 well plates and grown for 24 h at 37° C. in an atmosphere containing 5% CO$_2$. The medium was removed by aspiration, and 90 µl serum-free medium and 10 µl of siRNA/peptide complex solution were added. Cells were incubated for 4 h at 37° C./5% CO$_2$, 50 µl triple FCS medium were added, and the cells incubated for another 20 h under identical conditions. Subsequently, E6AP mRNA content was determined as described below.

For Lipofectamine2000™ transfections, 0.5 µl Lipofectamine2000™ were mixed with 12 µl OptiMem™ (Invitrogen, Karlsruhe, Germany, Cat. No. 11058-021) and incubated for 15 min. 1 µl of a 5 µM solution of the respective siRNA in PBS (Biochrom AG, Berlin, Germany, Cat-No: L182-05) were added to 11.5 µl OptiMeM™, mixed with the Lipofectamine2000™/OptiMem™ solution, and incubated for further 15 min. $1.5 \times 10^5$ HCT116-cells per well in 150 µl standard growth medium were grown for 24 h as described above, the growth medium removed from the cells by aspiration, and 75 µl fresh standard growth medium and the 25 µl of the siRNA/Lipofectamine2000™ mix were added to the well, to give a final siRNA concentration of 50 nM. The cells were incubated for 24 h at 37° C./5% $CO_2$ and E6AP mRNA concentration determined.

5.4. E6AP mRNA Quantitation

The QuantiGene™ bDNA-kit from Panomics, Inc., Fremont, USA, was used according to manufacturer's instructions. Briefly, cells were lysed by adding 50 µl of Lysis Mixture (from QuantiGene bDNA-kit) to each well and incubation at 53° C. for 1 h. 50 µl of the lysates were subsequently incubated with probes specific to human GAPDH and E6AP, respectively (sequence of probes given in Table 3 and ) according to the manufacturer's protocol for the QuantiGene bDNA kit assay. Finally, chemoluminescence is measured in a Victor2-Light (Perkin Elmer, Wiesbaden, Germany) as RLUs (relative light units) and values obtained with E6AP probes are normalized to the respective GAPDH values for each well. Mock transfected cells serve as controls and for normalization of mRNA levels (E6AP/GAPDH ratio in mock transfected cells is defined as 100% remaining E6AP-mRNA).

TABLE 5 bDNA probe set used in determination of human E6AP mRNA content in cells

| Function | Sequence | SEQ ID NO: |
|---|---|---|
| CE | TTTTCCCCATTAGCTTCCTGTATTTTTCTCTTGGAAAGAAAGT | 53 |
| CE | ACTCTGATATAGAACTGGGTGAGAGTCTTTTTCTCTTGGAAAGAAAGT | 54 |
| CE | AAAGATCTGTCTGTGATATCTGGAAATTTTTCTCTTGGAAAGAAAGT | 55 |
| CE | AATTCCTTCCTGTTTTCATTTGTAATTTTTTCTCTTGGAAAGAAAGT | 56 |
| CE | CCTTGAACTGTTTTTCTACTGATTTATTTTTTTCTCTTGGAAAGAAAGT | 57 |
| LE | CCCTTCATACTCCAATAAATCTTTTAATTTTTAGGCATAGGACCCGTGTCT | 58 |
| LE | TAGATCATACATCATTGGGTTACCAATTTTTAGGCATAGGACCCGTGTCT | 59 |
| LE | ACTTTAAGGGAGATTCATTGGTCATTTTTAGGCATAGGACCCGTGTCT | 60 |
| LE | CCGGCTTCCACATATAAGCAATTTTTAGGCATAGGACCCGTGTCT | 61 |
| LE | GTATAGCCACCGTCATATTCTGTAGTTTTTTAGGCATAGGACCCGTGTCT | 62 |
| BL | TCCCAAGTCACGAAAAGTTCCTT | 63 |
| BL | GTGATCATCATGTCATCTTCCACATT | 64 |
| BL | TGGAATTTTATCACCATTTTCCTT | 65 |
| BL | GAGAATGTAGTCAGAATAAAGATTGACA | 66 |
| BL | CCATATGAAAACCTCTCCGAAAAG | 67 |
| BL | TTCAATTTCTTCTGGTCTGAATAAGT | 68 |
| BL | TTCTTCTAGTGCTTGGAAATCTAGAT | 69 |
| BL | CCCTAATCAGAACAGAGTCCCTG | 70 |

6. Optimizing ppTG20

We obtained the 26 peptides shown in Table 6 with amino acid sequences based on ppTG20 but with the amino acid substitutions shown in Table 6, and evaluated their ability to mediate introduction of siRNA AD-8724 into HCT116 cells by monitoring inhibition of E6AP mRNA expression as described above. The concentration of the siRNA in these experiments was 250 nM, the molar peptide/siRNA ratio was 12.5:1.

TABLE 6

Peptides based on ppTG20 but comprising amino acid substitutions evaluated for their ability to mediate introduction of siRNA AD-8724 into HCT116 cells as evidenced by inhibition of E6AP mRNA expression

| Alnylam Peptide # | Amino acid sequence | Amino acid substitutions compared to parent peptide (ppTG20) | SEQ ID NO: | remaining E6AP mRNA (in % of mock) |
|---|---|---|---|---|
| Mock transfection | | | | 100 ± 16% |
| AP-1 | RLFFALLRLLRSLWRLLLRA | G1→ R | 71 | 27 ± 4% |
| AP-2 | GLFRALLRLLRSLWRLLRRA | L18→ R | 72 | 58 ± 7% |
| AP-3 | GLFRALLRLLRRLWRLLLRA | S12→ R | 73 | 43 ± 7% |
| AP-4 | RLFRALLRLLRSLWRLLRRA | G1/L18→ R | 74 | 34 ± 6% |
| AP-5 | GLFRALRRLLRSLWRLLRRA | L7/L18→ R | 75 | 108 ± 47% |
| AP-6 | RLFRALLRLLRRLWRLLLRA | G1/S12→ R | 76 | 41 ± 11% |
| AP-7 | RLFRALLRLLRRLWRLLRRA | G1/S12/L18→ R | 77 | 134 ± 19% |
| AP-8 | RLFRALRRLLRRLWRLLRRA | G1/S12/L7/L18→ R | 78 | 170 ± 44% |
| AP-9 | HLFRALLRLLRSLWRLLHRA | G1/L18→ H | 79 | 53 ± 17% |
| AP-10 | HLFRALLRLLRHLWRLLLRA | G1/S12→ H | 80 | 41 ± 21% |
| AP-11 | HLFRALLRLLRHLWRLLHRA | G1/S12/L18→ H | 81 | 62 ± 15% |
| AP-12 | HLFRALHRLLRHLWRLLHRA | G1/S12/L7/L18→ H | 82 | 94 ± 31% |
| AP-13 | HLFRALRRLLRHLWRLLRRA | L7/L18→ R, G1/S12→ H | 83 | 59 ± 7% |
| AP-14 | HLFRHLLRLLRRLWHLLHRA | G1/A5/R15/L18→ H, S12→ R | 84 | 56 ± 21% |
| AP-15 | HLFRHLLRLLRHLWRHLLRA | G1/A5/S12/L16→ H | 85 | 77 ± 39% |
| AP-16 | GLFFRALLRLLRSLWRLLSRA | L18→ S | 86 | 43 ± 13% |
| AP-17 | GLFRALLRLLRSLWRSLLRA | L16→ S | 87 | 37 ± 9% |
| AP-18 | GLFRALLRLLRSLWRSLSRA | L16/L18→ S | 88 | 49 ± 3% |
| AP-19 | GLYRALLRLLRSLWRLLLRA | F3→ Y | 89 | 27 ± 9% |
| AP-20 | GLYRALLRLLRSLWRLLSRA | F3→ Y, L18→ S | 90 | 45 ± 6% |
| AP-21 | GAFRAALRLLRSLWRLLLRA | L2/L6→ A | 91 | 53 ± 32% |
| AP-22 | GLFRALLRLLRSLWRALARA | L16/L18→ A | 92 | 32 ± 14% |
| AP-23 | GAFRAAARLLRSLWRLLLRA | L2/L6/L7→ A | 93 | 82 ± 6% |
| AP-24 | GAFRAAARLLRSLWRALLRA | L2/L6/L7/L16→ A | 94 | 91 ± 16% |
| AP-25 | GLFRALARALRSLWRALARA | L7/L9/L16/L18→ A | 95 | 83 ± 5% |
| AP-26 | GAYRAALRLLRSLWRLLSRA | L2/L6→ A, F3→ Y, L18→ S | 96 | 78 ± 6% |
| ppTG20 | GLFRALLRLLRSLWRLLLRA | Parent | 2 | 31 ± 9% |
| 50 nM AD-5107/LF[1] | | | | 79 ± 5% |
| 50 nM ND-8724/LF[1] | | | | 18 ± 5% |

[1] LF = Lipofectamine

Furthermore, we obtained a number of peptides comprising additional histidine caps on the C-terminus and/or the N-terminus, and compared their efficacy in mediating inhibition of E6AP mRNA expression with the corresponding peptides not comprising such histidine caps at different concentrations. Results are shown in Table 7.

TABLE 7

Peptides based on ppTG20, AP-1, AP-4, or AP-10, but comprising additional histidine caps, evaluated for their ability to mediate introduction of siRNA AD-8724 into HCT116 cells as evidenced by inhibition of E6AP mRNA expression

| Alnylam Peptide # | Amino acid sequence | SEQ ID NO: | Parent peptide | siRNA/ peptide conc. | remaining E6AP mRNA (in % of mock) |
|---|---|---|---|---|---|
| Mock transfection | | | | | 100 ± 27% |
| AP-0 | GLFRALLRLLRSLWRLLLRAHHHHH | 97 | ppTG20 | 250 nM/ 2 µM | 32 ± 3% |
| AP-1 | RLFRALLRLLRSLWRLLLRA | 71 | | 1 µM/ 10 µM | 17 ± 4% |
| AP-1 | " | | | 250 nM/ 2.5 µM | 36 ± 4% |
| AP-1 | " | | | 100 nM/ 800 nM | 54 ± 17% |
| AP-1 | " | | | 50 nM/ 400 nM | 72 ± 4% |
| AP-1 | " | | | 25 nM/ 250 nM | 100 ± 9% |
| AP-27 | RLFRALLRLLRSLWRLLLRAHHHHH | 98 | AP-1 | 1 µM/ 10 µM | 11 ± 2% |
| AP-27 | " | | | 250 nM/ 2.5 µM | 16 ± 3% |
| AP-27 | " | | | 250 nM/ 2.0 µM | 16 ± 3% |
| AP-27 | " | | | 100 nM/ 800 nM | 41 ± 6% |
| AP-27 | " | | | 50 nM/ 400 nM | 72 ± 9% |
| AP-27 | " | | | 25 nM/ 250 nM | 72 ± 13% |
| AP-4 | RLFRALLRLLRSLWRLLRRA | 74 | | 1 µM/ 10 µM | 37 ± 9% |
| AP-4 | " | | | 250 nM/ 2.5 µM | 49 ± 11% |
| AP-4 | " | | | 25 nM/ 250 nM | 96 ± 24% |
| AP-28 | RLFRALLRLLRSLWRLLRRAHHHHH | 99 | AP-4 | 1 µM/ 10 µM | 18 ± 2% |
| AP-28 | " | | | 250 nM/ 2.5 µM | 30 ± 9% |
| AP-28 | " | | | 25 nM/ 250 nM | 105 ± 13% |
| AP-10 | HLFRALLRLLRHLWRLLLRA | 80 | | 1 µM/ 10 µM | 17 ± 1% |
| AP-10 | " | | | 250 nM/ 2.5 µM | 28 ± 4% |
| AP-10 | " | | | 25 nM/ 250 nM | 98 ± 8% |

TABLE 7-continued

Peptides based on ppTG20, AP-1, AP-4, or AP-10, but comprising additional histidine caps, evaluated for their ability to mediate introduction of siRNA AD-8724 into HCT116 cells as evidenced by inhibition of E6AP mRNA expression

| Alnylam Peptide # | Amino acid sequence | SEQ ID NO: | Parent peptide | siRNA/ peptide conc. | remaining E6AP mRNA (in % of mock) |
|---|---|---|---|---|---|
| AP-29 | HLFRALLRLLRHLWRLLLRAHHHHH | 100 | AP-10 | 1 µM/ 10 µM | 11 ± 1% |
| AP-29 | " | | | 250 nM/ 2.5 µM | 16 ± 2% |
| AP-29 | " | | | 25 nM/ 250 nM | 58 ± 8% |
| AP-30 | HHHHHRLFRALLRLLRSLWRLLLRA | 101 | AP-1 | 250 nM/ 2.0 µM | 23 ± 2% |
| AP-30 | " | | | 100 nM/ 800 nM | 67 ± 6% |
| AP-30 | " | | | 50 nM/ 400 nM | 74 ± 9% |
| AP-32 | HHHHHRLFRALLRLLRSLWRLLLRA-HHHHH | 102 | AP-1 | 250 nM/ 2.0 µM | 23 ± 2% |
| AP-32 | HHHHHRLFRALLRLLRSLWRLLLRA-HHHHH | | | 100 nM/ 800 nM | 67 ± 6% |
| AP-32 | HHHHHRLFRALLRLLRSLWRLLLRA-HHHHH | | | 50 nM/ 400 nM | 74 ± 9% |
| AP-34 | RLFRALLRLLRSLWRLLLRA-HHHHHHHHHH | 103 | AP-1 | 250 nM/ 2.0 µM | 22 ± 5% |
| AP-34 | RLFRALLRLLRSLWRLLLRA-HHHHHHHHHH | | | 100 nM/ 800 nM | 52 ± 11% |
| AP-34 | RLFRALLRLLRSLWRLLLRA-HHHHHHHHHH | | | 50 nM/ 400 nM | 64 ± 12% |
| ppTG20 | GLFRALLRLLRSLWRLLLRA | 2 | | 250 nM/ 2.0 µM | 60 ± 10% |
| ppTG20 | " | | | 100 nM/ 800 nM | 94 ± 12% |
| ppTG20 | " | | | 50 nM/ 400 nM | 86 ± 10% |

Potential cytotoxic effects as mediator of inhibition were ruled out by determining cell viability in the presence of 2.5 µM of ppTG20, AP-0, AP-1, AP-27, AP-30, AP32 and AP-34 using the CytoTox ONE™ assay (Promega GmbH, Mannheim, Germany). None of these peptides led to a significant alteration of cell viability.

Evidently, appending 5, or preferably 10, or more, Histidine residues to the C-terminal end of ppTG20 significantly improves its ability to mediate cross membrane transport of anionic substances, particularly of siRNAs, while not compromising cell survival.

7. Determination of Optimal (Peptide):(Anionic Substance) Ratio

The optimal ratio of (peptide):(anionic substance) for complex formation, was determined in section 3 above to lie in the range of 8:1 to 13:1 by titrating a fixed concentration of the anionic substance with increasing amounts of the peptide, and monitoring complex formation by electrophoresis of the mixture. To further validate and possibly narrow down the optimum ratio of peptide/anionic substance, an assay with a functional readout was performed. HCT116 cells were incubated with siRNA complexes as described above at concentrations such that the amount of siRNA in the incubation mixture corresponds to a 250 nM concentration of the siRNA, and the peptide/siRNA ratio was 8:1, 10:1, 12:1, or 14:1.

TABLE 8

Influence of peptide/siRNA ratio on siRNA activity for different peptides

| | Remaining eGFP-mRNA in % of mock-transfected controls at peptide/siRNA ratio of | | | |
|---|---|---|---|---|
| Peptide # | 8:1 | 10:1 | 12:1 | 14:1 |
| AP-1 | 17 ± 5% | 18 ± 5% | 20 ± 6% | 21 ± 6% |
| AP-2 | 54 ± 6% | 35 ± 15% | 32 ± 11% | 36 ± 7% |

TABLE 8-continued

Influence of peptide/siRNA ratio on siRNA activity for different peptides

| Peptide # | Remaining eGFP-mRNA in % of mock-transfected controls at peptide/siRNA ratio of | | | |
|---|---|---|---|---|
| | 8:1 | 10:1 | 12:1 | 14:1 |
| AP-3 | 39 ± 10% | 32 ± 4% | 40 ± 5% | 40 ± 8% |
| AP-4 | 23 ± 6% | 18 ± 6% | 52 ± 6% | 43 ± 4% |
| AP-6 | 62 ± 9% | 36 ± 8% | 63 ± 18% | 54 ± 9% |
| AP-9 | 38 ± 6% | 31 ± 3% | 22 ± 1% | 36 ± 7% |
| AP-10 | 42 ± 3% | 24 ± 4% | 24 ± 2% | 32 ± 4% |
| AP-11 | 27 ± 5% | 30 ± 8% | 30 ± 5% | 24 ± 5% |
| AP-14 | 41 ± 2% | 41 ± 12% | 19 ± 2% | 39 ± 7% |
| AP-15 | 32 ± 5% | 26 + 2% | 22 ± 4% | 43 ± 5% |

8. Influence of Various Environmental Variables on the Capacity of CPPs to Mediate Cross Membrane Transport We investigated the influences of temperature, the presence of serum, and of certain substances that may effect cross-membrane transport in different manners. In addition, the stability of an siRNA was compared with and without complexing peptide.

HCT116 cells were treated with siRNA/peptide at 37° C. or 4° C., or at 37° C. in the presence of 10% FCS. For the 37° C. experiment HCT116 cells were incubated with 250 nM siRNA and an optimized AP molar excess. For the 4° C. experiment HCT116 cells and the same siRNA AP complexes were separately held at 4° C. for 1 h, then mixed and incubated for an additional hour at that temperature.

Alternatively, HCT116 cells were pretreated with a mixture of 10 mM NaN$_3$/2-Deoxyglucose (2-DeOGlc), 1 mM Methyl-β-cyclodextrin (MbCD) or 5 units/mL heparin for 30 min at 37° C. Then siRNA (250 nM) complexed with an optimized molar excess of ppTG-20, AP-0, AP-4 or AP-10 was added and target silencing was measured 24 h later.

TABLE 9

Influence of temperature on capacity for cross membrane transport of siRNA for selected peptides

| Peptide # | siRNA/peptide conc. | 37° C. | 4° C. |
|---|---|---|---|
| ppTG20 | 250 nM/3.13 μM | 15 ± 11% | 77 ± 15% |
| AP-0 | 250 nM/3.13 μM | 14 ± 1% | 45 ± 9% |
| AP-1 | 250 nM/2.0 μM | 13 ± 8% | 60 ± 6% |
| AP-4 | 250 nM/2.5 μM | 30 ± 5% RT | 56 ± 4% |
| AP-10 | 250 nM/2.5 μM | 13 ± 8% | 81 ± 16% |

Uptake was only partially attenuated when the temperature was reduced from 37° C. to 4° C. Moreover, uptake is largely unaffected by a metabolic inhibitor such as NaN3/2-Deoxyglucose. This may indicate a contribution of an energy independent mechanism to the overall up-take. Pretreatment of the cells with Methyl-β-cyclodextrin, a membrane cholesterol depleting agent, had a negligible effect on the uptake. Therefore, a lipid raft mediated uptake may not play a significant role.

The most pronounced inhibition of silencing was obtained by pretreatment with the polyanion heparin pointing to important electrostatic interactions between the CPP and the cell membrane, but still appreciable target silencing could be detected.

siRNA or an siRNA/peptide complex was incubated with mouse serum or rat cerebrospinal fluid for 0, 0.25, 0.5, 1, 2, 4 or 6 h, and remaining full length sense and antisense strand determined by HPLC/Mass Spectrometry. After 4 h, no full length strand remained from the naked siRNA in mouse serum, while 10-15% of both strands remained after 6 h incubation of the siRNA/peptide complex. In rat cerebrospinal fluid, 80-90% of full length strands remained from the naked siRNA, while 90-95% of full length strands remained after 6 h incubation of the siRNA/peptide complex.

CITED REFERENCES

Bartlett, G. R. 1959, J. Biol. Chem. 234, 466-469.
Gottschalk, S. et al., 1996, Gene Therapy 3 448-457.
Langle-Rouault et al. 1998. J. Virol. 72:6181-6185.
Mahato, R. I et al. 1999 Current Opinions in Molecular Therapeutics 1, 226-243.
Meyer, O. et al. (2000) Gene Therapy 7:1606-1611.
Olson, F et al., 1979 Biochim. Biophys. Acta 557, 19-23.
Planck, C. et al., 1994, J. Biol. Chem. 269, 12918-12924.
Wyman, T. B et al., 1997, Biochemistry 36: 3008-3017

We claim:

1. A peptide consisting of the amino acid sequence GLFXALLXLLXSLWXLLLXAZ$_1$Z$_2$Z$_3$Z$_4$ (SEQ ID NO:1), wherein each X is independently E, R, A, I, L, F, P, W, V, N, C, Q, G, S, T or Y, and wherein each of Z$_1$, Z$_2$, Z$_3$, and Z$_4$, is independently H, K, R, or Q.

2. The peptide of claim 1, wherein each X is independently E or R, and each of Z$_1$, Z$_2$, Z$_3$, and Z$_4$, is independently H, K, R, or Q.

3. The peptide of claim 1, wherein each X is independently E or R, and each of Z$_1$, Z$_2$, Z$_3$, and Z$_4$, is independently H, K, or R.

4. The peptide of claim 1, wherein each X is independently E or R, and each Z$_1$, Z$_2$, Z$_3$, and Z$_4$, is H.

5. The peptide of claim 1, wherein the peptide consists of one of the amino acid sequences of SEQ ID NO:3 to SEQ ID NO:7.

6. The peptide of claim 1, wherein said peptide is capable of: causing cell membrane disruption, binding to an anionic substance, and enhancing the transfer of said anionic substance into a cell.

7. The peptide of claim 6, wherein said anionic substance is a nucleic acid that mediates RNA interference and said peptide is capable of enhancing said RNA interference.

8. The peptide of claim 6, wherein said anionic substance comprises genetic information that may be expressed by a cell and said peptide is capable of enhancing the expression of said genetic information from said anionic substance.

9. A composition comprising a complex of (i) the peptide of claim 1, and (ii) at least one anionic substance.

10. The composition of claim 9, wherein the molar ratio peptide:anionic substance in the complex is between 8:1 and 13:1.

11. The composition of claim 9, wherein the anionic substance is a nucleic acid that mediates RNA interference and said peptide is capable of enhancing said RNA interference.

12. The composition of claim 9, further comprising: (iii) at least one ligand capable of cell-specific and/or nuclear targeting; (iv) at least one peptide capable of causing membrane disruption; (v) at least one cationic compound selected from the group consisting of: cationic lipids and cationic polymers, and/or (vi) a colipid.

13. The composition of claim 9 or 12, further comprising: a pharmaceutical carrier.

14. A method for manufacturing a composition of claim 9, comprising the steps of (a) contacting at least one peptide of claim 1 with an anionic substance, wherein said contacting forms a complex between said anionic substance and said peptide; and (b) recovering said complex.

15. The method of claim 14, further comprising the step of formulating the complex with a pharmaceutical carrier.

16. A method of introducing an anionic substance into a cell, comprising the steps of: (1) contacting the anionic substance with a peptide of claim 1, wherein said contacting forms a complex between said anionic substance and said peptide; and (2) contacting said cell with said complex.

17. A peptide comprising an amino acid sequence of the formula GLFRALLRLLRSLWRLLLRA (SEQ ID NO:2), said amino acid sequence being modified by one or more of the substitutions: G1→R, L18→R, S12→R, L7→R, G1→H, L18→H, S12→H, L7→H, A5→H, R15→H, L16→H, L18→S, L16→S, F3→Y, L2→A, L6→A, L16→A, L18→A, and L9→A, and further comprising up to 5 histidine residues to the N-terminus and/or the C-terminus.

18. A peptide comprising an amino acid sequence of one of:
AP-0 (SEQ ID NO:97), AP-1 (SEQ ID NO: 71), AP-2 (SEQ ID NO: 72), AP-3 (SEQ ID NO: 73), AP-4 (SEQ ID NO: 74), AP-5 (SEQ ID NO: 75), AP-6 (SEQ ID NO: 76), AP-7 (SEQ ID NO: 77), AP-8 (SEQ ID NO: 78), AP-9 (SEQ ID NO: 79), AP-10 (SEQ ID NO: 80), AP-11 (SEQ ID NO: 81), AP-12 (SEQ ID NO: 82), AP-13 (SEQ ID NO: 83), AP-14 (SEQ ID NO: 84), AP-15 (SEQ ID NO: 85), AP-16 (SEQ ID NO: 86), AP-17 (SEQ ID NO: 87), AP-18 (SEQ ID NO: 88), AP-19 (SEQ ID NO: 89), AP-20 (SEQ ID NO: 90), AP-21 (SEQ ID NO: 91), AP-22 (SEQ ID NO: 92), AP-23 (SEQ ID NO: 93), AP-24 (SEQ ID NO: 94), AP-25 (SEQ ID NO: 95), AP-26 (SEQ ID NO: 96), AP-27 (SEQ ID NO: 98), AP-28 (SEQ ID NO: 99), AP-29 (SEQ ID NO: 100), AP-30 (SEQ ID NO: 101), AP-32 (SEQ ID NO: 102), or AP-34 (SEQ ID NO: 103).

19. The peptide of claim 18, wherein the peptide is one of AP-1 (SEQ ID NO: 71), AP-4 (SEQ ID NO: 74), or AP-10 (SEQ ID NO: 80).

20. The method of claim 14 or 16, wherein said anionic substance is a nucleic acid that mediates RNA interference and said peptide is capable of enhancing said RNA interference.

* * * * *

SEQUENCE LISTING

```
<160> NUMBER OF SEQ ID NOS: 103

<210> SEQ ID NO 1
<211> LENGTH: 24
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 4, 8, 11, 15, 19
<223> OTHER INFORMATION: Xaa = Glu, Arg, Ala , Ile , Leu, Phe, Pro,
      Trp, Val, Asn, Cys, Gln, Gly , Ser, Thr or
      Tyr
<220> FEATURE:
<221> NAME/KEY: VARIANT
<222> LOCATION: 21, 22, 23, 24
<223> OTHER INFORMATION: Xaa = His, Lys, Arg, or Gln

<400> SEQUENCE: 1

Gly Leu Phe Xaa Ala Leu Leu Xaa Leu Leu Xaa Ser Leu Trp Xaa Leu
```

```
                1               5                   10                  15
Leu Leu Xaa Ala Xaa Xaa Xaa Xaa
            20
```

<210> SEQ ID NO 2
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 2

```
Gly Leu Phe Arg Ala Leu Leu Arg Leu Leu Arg Ser Leu Trp Arg Leu
 1               5                   10                  15
Leu Leu Arg Ala
            20
```

<210> SEQ ID NO 3
<211> LENGTH: 24
<212> TYPE: PRT
<213> ORGANISM: Artificial Sequence
<220> FEATURE:
<223> OTHER INFORMATION: Synthetically generated peptide

<400> SEQUENCE: 3

```
Gly Leu Phe Arg Ala Leu Leu Arg Leu Leu Arg Ser Leu Trp Arg Leu
 1               5                   10                  15
Leu Leu Arg Ala His His His His
            20
```

<210> SEQ ID NO 4
<211> LENGTH: 24
<212> TYPE: PRT
<213> ORGANISM: Artificial Sequence
<220> FEATURE:
<223> OTHER INFORMATION: Synthetically generated peptide

<400> SEQUENCE: 4

```
Gly Leu Phe Arg Ala Leu Leu Arg Leu Leu Arg Ser Leu Trp Arg Leu
 1               5                   10                  15
Leu Leu Arg Ala Arg Arg Arg Arg
            20
```

<210> SEQ ID NO 5
<211> LENGTH: 24
<212> TYPE: PRT
<213> ORGANISM: Artificial Sequence
<220> FEATURE:
<223> OTHER INFORMATION: Synthetically generated peptide

<400> SEQUENCE: 5

```
Gly Leu Phe Arg Ala Leu Leu Arg Leu Leu Arg Ser Leu Trp Arg Leu
 1               5                   10                  15
Leu Leu Arg Ala Leu Leu Leu Leu
            20
```

<210> SEQ ID NO 6
<211> LENGTH: 24
<212> TYPE: PRT
<213> ORGANISM: Artificial Sequence
<220> FEATURE:
<223> OTHER INFORMATION: Synthetically generated peptide

<400> SEQUENCE: 6

```
Gly Leu Phe Glu Ala Leu Leu Glu Leu Leu Glu Ser Leu Trp Glu Leu
```

```
                1               5                   10                  15
Leu Leu Glu Ala His His His His
            20

<210> SEQ ID NO 7
<211> LENGTH: 24
<212> TYPE: PRT
<213> ORGANISM: Artificial Sequence
<220> FEATURE:
<223> OTHER INFORMATION: Synthetically generated peptide

<400> SEQUENCE: 7

Gly Leu Phe Glu Ala Leu Leu Glu Leu Leu Glu Ser Leu Trp Glu Leu
 1               5                   10                  15

Leu Leu Glu Ala Arg Arg Arg Arg
            20

<210> SEQ ID NO 8
<211> LENGTH: 24
<212> TYPE: PRT
<213> ORGANISM: Artificial Sequence
<220> FEATURE:
<223> OTHER INFORMATION: Synthetically generated peptide

<400> SEQUENCE: 8

Gly Leu Phe Glu Ala Leu Leu Glu Leu Leu Glu Ser Leu Trp Glu Leu
 1               5                   10                  15

Leu Leu Glu Ala Leu Leu Leu Leu
            20

<210> SEQ ID NO 9
<211> LENGTH: 16
<212> TYPE: PRT
<213> ORGANISM: Artificial Sequence
<220> FEATURE:
<223> OTHER INFORMATION: Cell penetrating peptides

<400> SEQUENCE: 9

Arg Gln Ile Lys Ile Trp Phe Gln Asn Arg Arg Met Lys Trp Lys Lys
 1               5                   10                  15

<210> SEQ ID NO 10
<211> LENGTH: 17
<212> TYPE: PRT
<213> ORGANISM: Artificial Sequence
<220> FEATURE:
<223> OTHER INFORMATION: Cell penetrating peptides

<400> SEQUENCE: 10

Arg Gln Ile Lys Ile Trp Phe Gln Asn Arg Arg Met Lys Trp Lys Lys
 1               5                   10                  15

Cys

<210> SEQ ID NO 11
<211> LENGTH: 21
<212> TYPE: PRT
<213> ORGANISM: Artificial Sequence
<220> FEATURE:
<223> OTHER INFORMATION: Cell penetrating peptides
<220> FEATURE:
<221> NAME/KEY: AMIDATION
<222> LOCATION: 21
<223> OTHER INFORMATION: Conjugated amide

<400> SEQUENCE: 11

Ala Gly Tyr Leu Leu Gly Lys Ile Asn Leu Lys Ala Leu Ala Ala Leu
```

```
                1               5                  10                 15
Ala Lys Lys Ile Leu
            20

<210> SEQ ID NO 12
<211> LENGTH: 24
<212> TYPE: PRT
<213> ORGANISM: Artificial Sequence
<220> FEATURE:
<223> OTHER INFORMATION: Cell penetrating peptides
<220> FEATURE:
<221> NAME/KEY: AMIDATION
<222> LOCATION: 24
<223> OTHER INFORMATION: Conjugated amide

<400> SEQUENCE: 12

Gly Ala Leu Phe Leu Gly Trp Leu Gly Ala Ala Gly Ser Thr Met Gly
  1               5                  10                 15

Ala Pro Lys Lys Lys Arg Lys Val
            20

<210> SEQ ID NO 13
<211> LENGTH: 20
<212> TYPE: PRT
<213> ORGANISM: Artificial Sequence
<220> FEATURE:
<223> OTHER INFORMATION: Cell penetrating peptides

<400> SEQUENCE: 13

Gly Leu Phe Lys Ala Leu Leu Lys Leu Leu Lys Ser Leu Trp Lys Leu
  1               5                  10                 15

Leu Leu Lys Ala
            20

<210> SEQ ID NO 14
<211> LENGTH: 20
<212> TYPE: PRT
<213> ORGANISM: Artificial Sequence
<220> FEATURE:
<223> OTHER INFORMATION: Cell penetrating peptides

<400> SEQUENCE: 14

Gly Leu Phe Arg Ala Leu Leu Arg Leu Leu Arg Ser Leu Trp Arg Leu
  1               5                  10                 15

Leu Leu Arg Ala
            20

<210> SEQ ID NO 15
<211> LENGTH: 21
<212> TYPE: PRT
<213> ORGANISM: Artificial Sequence
<220> FEATURE:
<223> OTHER INFORMATION: Cell penetrating peptides

<400> SEQUENCE: 15

Cys Gly Leu Phe Arg Ala Leu Leu Arg Leu Leu Arg Ser Leu Trp Arg
  1               5                  10                 15

Leu Leu Leu Arg Ala
            20

<210> SEQ ID NO 16
<211> LENGTH: 8
<212> TYPE: PRT
<213> ORGANISM: Artificial Sequence
<220> FEATURE:
<223> OTHER INFORMATION: Cell penetrating peptides
```

```
<400> SEQUENCE: 16

Arg Arg Arg Arg Arg Arg Arg Arg
 1               5

<210> SEQ ID NO 17
<211> LENGTH: 11
<212> TYPE: PRT
<213> ORGANISM: Artificial Sequence
<220> FEATURE:
<223> OTHER INFORMATION: Cell penetrating peptides

<400> SEQUENCE: 17

Tyr Ala Arg Val Arg Arg Arg Gly Pro Arg Arg
 1               5                  10

<210> SEQ ID NO 18
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 18
ccacaugaag cagcacgacu u                                              21

<210> SEQ ID NO 19
<211> LENGTH: 21
<212> TYPE: RNA
<213> ORGANISM: Artificial Sequence
<220> FEATURE:
<223> OTHER INFORMATION: Synthetically generated  siRNA
<220> FEATURE:
<221> NAME/KEY: modified_base
<222> LOCATION: 21
<223> OTHER INFORMATION: 2'-O-methyl-ribonucleotide, phosphorothioate
      backbone linkage

<400> SEQUENCE: 19
aagucgugcu gcuucaugug g                                              21

<210> SEQ ID NO 20
<211> LENGTH: 21
<212> TYPE: DNA
<213> ORGANISM: Artificial Sequence
<220> FEATURE:
<223> OTHER INFORMATION: Synthetically generated siRNA

<400> SEQUENCE: 20
gucucccucu gucacgaugt t                                              21

<210> SEQ ID NO 21
<211> LENGTH: 21
<212> TYPE: DNA
<213> ORGANISM: Artificial Sequence
<220> FEATURE:
<223> OTHER INFORMATION: Synthetically generated siRNA

<400> SEQUENCE: 21
caucgugaca gagggagact t                                              21

<210> SEQ ID NO 22
<211> LENGTH: 42
<212> TYPE: DNA
<213> ORGANISM: Artificial Sequence
<220> FEATURE:
<223> OTHER INFORMATION: bDNA probe used in determination of human
      ENaC-alpha mRNA content in cells
```

-continued

<210> SEQ ID NO 22
<211> LENGTH: 42
<212> TYPE: DNA
<213> ORGANISM: Artificial Sequence
<220> FEATURE:
<223> OTHER INFORMATION: bDNA probe used in determination of human
      ENaC-alpha mRNA content in cells

<400> SEQUENCE: 22
gtctgtccag ggtttccttc cttttctct tggaaagaaa gt                    42

<210> SEQ ID NO 23
<211> LENGTH: 41
<212> TYPE: DNA
<213> ORGANISM: Artificial Sequence
<220> FEATURE:
<223> OTHER INFORMATION: bDNA probe used in determination of human
      ENaC-alpha mRNA content in cells

<400> SEQUENCE: 23
actgccattc ttggtgcagt tttttctctt ggaaagaaag t                    41

<210> SEQ ID NO 24
<211> LENGTH: 45
<212> TYPE: DNA
<213> ORGANISM: Artificial Sequence
<220> FEATURE:
<223> OTHER INFORMATION: bDNA probe used in determination of human
      ENaC-alpha mRNA content in cells

<400> SEQUENCE: 24
ctctcctgga agcaggagtg aatattttc tcttggaaag aaagt                 45

<210> SEQ ID NO 25
<211> LENGTH: 42
<212> TYPE: DNA
<213> ORGANISM: Artificial Sequence
<220> FEATURE:
<223> OTHER INFORMATION: bDNA probe used in determination of human
      ENaC-alpha mRNA content in cells

<400> SEQUENCE: 25
gccgcggata gaagatgtag gtttttctct tggaaagaaa gt                   42

<210> SEQ ID NO 26
<211> LENGTH: 42
<212> TYPE: DNA
<213> ORGANISM: Artificial Sequence
<220> FEATURE:
<223> OTHER INFORMATION: bDNA probe used in determination of human
      ENaC-alpha mRNA content in cells

<400> SEQUENCE: 26
gcacttggtg aaacagccca gtttttctct tggaaagaaa gt                   42

<210> SEQ ID NO 27
<211> LENGTH: 43
<212> TYPE: DNA
<213> ORGANISM: Artificial Sequence
<220> FEATURE:
<223> OTHER INFORMATION: bDNA probe used in determination of human
      ENaC-alpha mRNA content in cells

<400> SEQUENCE: 27
agcagagagc tggtagctgg tcttttctc ttggaaagaa agt                   43

<210> SEQ ID NO 28
<211> LENGTH: 42
<212> TYPE: DNA
<213> ORGANISM: Artificial Sequence
<220> FEATURE:
<223> OTHER INFORMATION: bDNA probe used in determination of human
      ENaC-alpha mRNA content in cells

<400> SEQUENCE: 28
cgccataatc gcccccaatt tttaggcata ggacccgtgt ct                              42

<210> SEQ ID NO 29
<211> LENGTH: 47
<212> TYPE: DNA
<213> ORGANISM: Artificial Sequence
<220> FEATURE:
<223> OTHER INFORMATION: bDNA probe used in determination of human
      ENaC-alpha mRNA content in cells

<400> SEQUENCE: 29
cacagccaca ctccttgatc atgttttag gcataggacc cgtgtct                          47

<210> SEQ ID NO 30
<211> LENGTH: 44
<212> TYPE: DNA
<213> ORGANISM: Artificial Sequence
<220> FEATURE:
<223> OTHER INFORMATION: bDNA probe used in determination of human
      ENaC-alpha mRNA content in cells

<400> SEQUENCE: 30
acagtactcc acgttctggg tttttaggca taggacccgt gtct                            44

<210> SEQ ID NO 31
<211> LENGTH: 47
<212> TYPE: DNA
<213> ORGANISM: Artificial Sequence
<220> FEATURE:
<223> OTHER INFORMATION: bDNA probe used in determination of human
      ENaC-alpha mRNA content in cells

<400> SEQUENCE: 31
ggagcttata gtagcagtac cccttttag gcataggacc cgtgtct                          47

<210> SEQ ID NO 32
<211> LENGTH: 41
<212> TYPE: DNA
<213> ORGANISM: Artificial Sequence
<220> FEATURE:
<223> OTHER INFORMATION: bDNA probe used in determination of human
      ENaC-alpha mRNA content in cells

<400> SEQUENCE: 32
acgctgcatg gcttccgttt ttaggcatag gacccgtgtc t                               41

<210> SEQ ID NO 33
<211> LENGTH: 44
<212> TYPE: DNA
<213> ORGANISM: Artificial Sequence
<220> FEATURE:
<223> OTHER INFORMATION: bDNA probe used in determination of human
      ENaC-alpha mRNA content in cells

<400> SEQUENCE: 33
gagggccatc gtgagtaacc tttttaggca taggacccgt gtct                            44

<210> SEQ ID NO 34
<211> LENGTH: 21
<212> TYPE: DNA
<213> ORGANISM: Artificial Sequence
<220> FEATURE:
<223> OTHER INFORMATION: bDNA probe used in determination of human
      ENaC-alpha mRNA content in cells

<400> SEQUENCE: 34
tcatgctgat ggaggtctcc a                                                     21

<210> SEQ ID NO 35
<211> LENGTH: 25
<212> TYPE: DNA
<213> ORGANISM: Artificial Sequence
<220> FEATURE:
<223> OTHER INFORMATION: bDNA probe used in determination of human
      ENaC-alpha mRNA content in cells

<400> SEQUENCE: 35
ggtaaaggtt ctcaacagga acatc                                              25

<210> SEQ ID NO 36
<211> LENGTH: 25
<212> TYPE: DNA
<213> ORGANISM: Artificial Sequence
<220> FEATURE:
<223> OTHER INFORMATION: bDNA probe used in determination of human
      ENaC-alpha mRNA content in cells

<400> SEQUENCE: 36
cacacctgct gtgtgtactt tgaag                                              25

<210> SEQ ID NO 37
<211> LENGTH: 23
<212> TYPE: DNA
<213> ORGANISM: Artificial Sequence
<220> FEATURE:
<223> OTHER INFORMATION: bDNA probe used in determination of human
      ENaC-alpha mRNA content in cells

<400> SEQUENCE: 37
caggaactgt gctttctgta gtc                                                23

<210> SEQ ID NO 38
<211> LENGTH: 23
<212> TYPE: DNA
<213> ORGANISM: Artificial Sequence
<220> FEATURE:
<223> OTHER INFORMATION: bDNA probe used in determination of human
      ENaC-alpha mRNA content in cells

<400> SEQUENCE: 38
gtggtctgag gagaagtcaa cct                                                23

<210> SEQ ID NO 39
<211> LENGTH: 19
<212> TYPE: DNA
<213> ORGANISM: Artificial Sequence
<220> FEATURE:
<223> OTHER INFORMATION: bDNA probe used in determination of human
      ENaC-alpha mRNA content in cells

<400> SEQUENCE: 39
ccattcctgg gatgtcacc                                                     19

<210> SEQ ID NO 40
<211> LENGTH: 41
<212> TYPE: DNA
<213> ORGANISM: Artificial Sequence
<220> FEATURE:
<223> OTHER INFORMATION: bDNA probe used in  determination of human
      GAPDH mRNA content in cells

<400> SEQUENCE: 40
gaatttgcca tgggtggaat tttttctctt ggaaagaaag t                            41

```
<210> SEQ ID NO 41
<211> LENGTH: 41
<212> TYPE: DNA
<213> ORGANISM: Artificial Sequence
<220> FEATURE:
<223> OTHER INFORMATION: bDNA probe used in  determination of human
      GAPDH mRNA content in cells

<400> SEQUENCE: 41
ggagggatct cgctcctgga tttttctctt ggaaagaaag t                41

<210> SEQ ID NO 42
<211> LENGTH: 40
<212> TYPE: DNA
<213> ORGANISM: Artificial Sequence
<220> FEATURE:
<223> OTHER INFORMATION: bDNA probe used in  determination of human
      GAPDH mRNA content in cells

<400> SEQUENCE: 42
ccccagcctt ctccatggtt tttctcttg gaaagaaagt                 40

<210> SEQ ID NO 43
<211> LENGTH: 40
<212> TYPE: DNA
<213> ORGANISM: Artificial Sequence
<220> FEATURE:
<223> OTHER INFORMATION: bDNA probe used in  determination of human
      GAPDH mRNA content in cells

<400> SEQUENCE: 43 gctccccct gcaaatgagt tttctcttg gaaagaaagt                  40

<210> SEQ ID NO 44
<211> LENGTH: 42
<212> TYPE: DNA
<213> ORGANISM: Artificial Sequence
<220> FEATURE:
<223> OTHER INFORMATION: bDNA probe used in  determination of human
      GAPDH mRNA content in cells

<400> SEQUENCE: 44
agccttgacg gtgccatgtt tttaggcata ggacccgtgt ct              42

<210> SEQ ID NO 45
<211> LENGTH: 45
<212> TYPE: DNA
<213> ORGANISM: Artificial Sequence
<220> FEATURE:
<223> OTHER INFORMATION: bDNA probe used in  determination of human
      GAPDH mRNA content in cells

<400> SEQUENCE: 45
gatgacaagc ttcccgttct ctttttaggc ataggacccg tgtct           45

<210> SEQ ID NO 46
<211> LENGTH: 46
<212> TYPE: DNA
<213> ORGANISM: Artificial Sequence
<220> FEATURE:
<223> OTHER INFORMATION: bDNA probe used in  determination of human
      GAPDH mRNA content in cells

<400> SEQUENCE: 46
agatggtgat gggatttcca ttttttaggc ataggaccc gtgtct           46

<210> SEQ ID NO 47
<211> LENGTH: 44
```

```
-continued

<212> TYPE: DNA
<213> ORGANISM: Artificial Sequence
<220> FEATURE:
<223> OTHER INFORMATION: bDNA probe used in determination of human
      GAPDH mRNA content in cells

<400> SEQUENCE: 47
gcatcgcccc acttgatttt tttttaggca taggacccgt gtct                44

<210> SEQ ID NO 48
<211> LENGTH: 43
<212> TYPE: DNA
<213> ORGANISM: Artificial Sequence
<220> FEATURE:
<223> OTHER INFORMATION: bDNA probe used in determination of human
      GAPDH mRNA content in cells

<400> SEQUENCE: 48
cacgacgtac tcagcgccat ttttaggcat aggacccgtg tct                 43

<210> SEQ ID NO 49
<211> LENGTH: 46
<212> TYPE: DNA
<213> ORGANISM: Artificial Sequence
<220> FEATURE:
<223> OTHER INFORMATION: bDNA probe used in determination of human
      GAPDH mRNA content in cells

<400> SEQUENCE: 49
ggcagagatg atgacccttt tgttttagg cataggaccc gtgtct               46

<210> SEQ ID NO 50
<211> LENGTH: 21
<212> TYPE: DNA
<213> ORGANISM: Artificial Sequence
<220> FEATURE:
<223> OTHER INFORMATION: bDNA probe used in determination of human
      GAPDH mRNA content in cells

<400> SEQUENCE: 50
ggtgaagacg ccagtggact c                                         21

<210> SEQ ID NO 51
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = thymidine phosphorothioate backbone
      linkage

<400> SEQUENCE: 51
ucacauucca cguuaggugt n                                         21

<210> SEQ ID NO 52
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = thymidine phosphorothioate backbone
      linkage

<400> SEQUENCE: 52
```
caccuaacgu ggaaugugat n                                              21

<210> SEQ ID NO 53
<211> LENGTH: 43
<212> TYPE: DNA
<213> ORGANISM: Artificial Sequence
<220> FEATURE:
<223> OTHER INFORMATION: bDNA probe used in determination of human E6AP
      mRNA content in cells

<400> SEQUENCE: 53
ttttccccat tagcttcctg tattttctc ttggaaagaa agt                        43

<210> SEQ ID NO 54
<211> LENGTH: 48
<212> TYPE: DNA
<213> ORGANISM: Artificial Sequence
<220> FEATURE:
<223> OTHER INFORMATION: bDNA probe used in determination of human E6AP
      mRNA content in cells

<400> SEQUENCE: 54
actctgatat agaactgggt gagagtcttt ttctcttgga aagaaagt                  48

<210> SEQ ID NO 55
<211> LENGTH: 47
<212> TYPE: DNA
<213> ORGANISM: Artificial Sequence
<220> FEATURE:
<223> OTHER INFORMATION: bDNA probe used in determination of human E6AP
      mRNA content in cells

<400> SEQUENCE: 55
aaagatctgt ctgtgatatc tggaaatttt tctcttggaa agaaagt                   47

<210> SEQ ID NO 56
<211> LENGTH: 47
<212> TYPE: DNA
<213> ORGANISM: Artificial Sequence
<220> FEATURE:
<223> OTHER INFORMATION: bDNA probe used in determination of human E6AP
      mRNA content in cells

<400> SEQUENCE: 56
aattccttcc tgttttcatt tgtaatttt tctcttggaa agaaagt                    47

<210> SEQ ID NO 57
<211> LENGTH: 49
<212> TYPE: DNA
<213> ORGANISM: Artificial Sequence
<220> FEATURE:
<223> OTHER INFORMATION: bDNA probe used in determination of human E6AP
      mRNA content in cells

<400> SEQUENCE: 57
ccttgaactg ttttctact gatttatttt tttctcttgg aaagaaagt                  49

<210> SEQ ID NO 58
<211> LENGTH: 51
<212> TYPE: DNA
<213> ORGANISM: Artificial Sequence
<220> FEATURE:
<223> OTHER INFORMATION: bDNA probe used in determination of human E6AP
      mRNA content in cells

<400> SEQUENCE: 58
cccttcatac tccaataaat cttttaattt ttaggcatag gacccgtgtc t              51

<210> SEQ ID NO 59
<211> LENGTH: 50
<212> TYPE: DNA
<213> ORGANISM: Artificial Sequence
<220> FEATURE:
<223> OTHER INFORMATION: bDNA probe used in determination of human E6AP
      mRNA content in cells

<400> SEQUENCE: 59
tagatcatac atcattgggt taccaatttt taggcatagg acccgtgtct           50

<210> SEQ ID NO 60
<211> LENGTH: 48
<212> TYPE: DNA
<213> ORGANISM: Artificial Sequence
<220> FEATURE:
<223> OTHER INFORMATION: bDNA probe used in determination of human E6AP
      mRNA content in cells

<400> SEQUENCE: 60
actttaaggg agattcattg gtcatttta ggcataggac ccgtgtct              48

<210> SEQ ID NO 61
<211> LENGTH: 45
<212> TYPE: DNA
<213> ORGANISM: Artificial Sequence
<220> FEATURE:
<223> OTHER INFORMATION: bDNA probe used in determination of human E6AP
      mRNA content in cells

<400> SEQUENCE: 61
ccggcttcca catataagca atttttaggc ataggacccg tgtct                45

<210> SEQ ID NO 62
<211> LENGTH: 50
<212> TYPE: DNA
<213> ORGANISM: Artificial Sequence
<220> FEATURE:
<223> OTHER INFORMATION: bDNA probe used in determination of human E6AP
      mRNA content in cells

<400> SEQUENCE: 62
gtatagccac cgtcatattc tgtagttttt taggcatagg acccgtgtct           50

<210> SEQ ID NO 63
<211> LENGTH: 23
<212> TYPE: DNA
<213> ORGANISM: Artificial Sequence
<220> FEATURE:
<223> OTHER INFORMATION: bDNA probe used in determination of human E6AP
      mRNA content in cells

<400> SEQUENCE: 63
tcccaagtca cgaaaagttc ctt                                        23

<210> SEQ ID NO 64
<211> LENGTH: 26
<212> TYPE: DNA
<213> ORGANISM: Artificial Sequence
<220> FEATURE:
<223> OTHER INFORMATION: bDNA probe used in determination of human E6AP
      mRNA content in cells

<400> SEQUENCE: 64
gtgatcatca tgtcatcttc cacatt                                     26

-continued

<210> SEQ ID NO 65
<211> LENGTH: 24
<212> TYPE: DNA
<213> ORGANISM: Artificial Sequence
<220> FEATURE:
<223> OTHER INFORMATION: bDNA probe used in determination of human E6AP
      mRNA content in cells

<400> SEQUENCE: 65 tggaattta tcaccatttt cctt                                              24

<210> SEQ ID NO 66
<211> LENGTH: 28
<212> TYPE: DNA
<213> ORGANISM: Artificial Sequence
<220> FEATURE:
<223> OTHER INFORMATION: bDNA probe used in determination of human E6AP
      mRNA content in cells

<400> SEQUENCE: 66
gagaatgtag tcagaataaa gattgaca                                         28

<210> SEQ ID NO 67
<211> LENGTH: 24
<212> TYPE: DNA
<213> ORGANISM: Artificial Sequence
<220> FEATURE:
<223> OTHER INFORMATION: bDNA probe used in determination of human E6AP
      mRNA content in cells

<400> SEQUENCE: 67
ccatatgaaa acctctccga aaag                                             24

<210> SEQ ID NO 68
<211> LENGTH: 26
<212> TYPE: DNA
<213> ORGANISM: Artificial Sequence
<220> FEATURE:
<223> OTHER INFORMATION: bDNA probe used in determination of human E6AP
      mRNA content in cells

<400> SEQUENCE: 68
ttcaatttct tctggtctga ataagt                                           26

<210> SEQ ID NO 69
<211> LENGTH: 26
<212> TYPE: DNA
<213> ORGANISM: Artificial Sequence
<220> FEATURE:
<223> OTHER INFORMATION: bDNA probe used in determination of human E6AP
      mRNA content in cells

<400> SEQUENCE: 69
ttcttctagt gcttggaaat ctagat                                           26

<210> SEQ ID NO 70
<211> LENGTH: 23
<212> TYPE: DNA
<213> ORGANISM: Artificial Sequence
<220> FEATURE:
<223> OTHER INFORMATION: bDNA probe used in determination of human E6AP
      mRNA content in cells

<400> SEQUENCE: 70
ccctaatcag aacagagtcc ctg                                              23

<210> SEQ ID NO 71
<211> LENGTH: 20

```
<212> TYPE: PRT
<213> ORGANISM: Artificial Sequence
<220> FEATURE:
<223> OTHER INFORMATION: Synthetically generated peptide

<400> SEQUENCE: 71

Arg Leu Phe Arg Ala Leu Leu Arg Leu Leu Arg Ser Leu Trp Arg Leu
 1               5                  10                  15

Leu Leu Arg Ala
         20

<210> SEQ ID NO 72
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 72

Gly Leu Phe Arg Ala Leu Leu Arg Leu Leu Arg Ser Leu Trp Arg Leu
 1               5                  10                  15

Leu Arg Arg Ala
         20

<210> SEQ ID NO 73
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 73

Gly Leu Phe Arg Ala Leu Leu Arg Leu Leu Arg Arg Leu Trp Arg Leu
 1               5                  10                  15

Leu Leu Arg Ala
         20

<210> SEQ ID NO 74
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 74

Arg Leu Phe Arg Ala Leu Leu Arg Leu Leu Arg Ser Leu Trp Arg Leu
 1               5                  10                  15

Leu Arg Arg Ala
         20

<210> SEQ ID NO 75
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 75

Gly Leu Phe Arg Ala Leu Arg Arg Leu Leu Arg Ser Leu Trp Arg Leu
 1               5                  10                  15

Leu Arg Arg Ala
         20

<210> SEQ ID NO 76
<211> LENGTH: 20
```

```
<212> TYPE: PRT
<213> ORGANISM: Artificial Sequence
<220> FEATURE:
<223> OTHER INFORMATION: Synthetically generated peptide

<400> SEQUENCE: 76

Arg Leu Phe Arg Ala Leu Leu Arg Leu Leu Arg Arg Leu Trp Arg Leu
 1               5                  10                  15

Leu Leu Arg Ala
         20

<210> SEQ ID NO 77
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 77

Arg Leu Phe Arg Ala Leu Leu Arg Leu Leu Arg Arg Leu Trp Arg Leu
 1               5                  10                  15

Leu Arg Arg Ala
         20

<210> SEQ ID NO 78
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 78

Arg Leu Phe Arg Ala Leu Arg Arg Leu Leu Arg Arg Leu Trp Arg Leu
 1               5                  10                  15

Leu Arg Arg Ala
         20

<210> SEQ ID NO 79
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 79

His Leu Phe Arg Ala Leu Leu Arg Leu Leu Arg Ser Leu Trp Arg Leu
 1               5                  10                  15

Leu His Arg Ala
         20

<210> SEQ ID NO 80
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 80

His Leu Phe Arg Ala Leu Leu Arg Leu Leu Arg His Leu Trp Arg Leu
 1               5                  10                  15

Leu Leu Arg Ala
         20

<210> SEQ ID NO 81
<211> LENGTH: 20
```

```
<212> TYPE: PRT
<213> ORGANISM: Artificial Sequence
<220> FEATURE:
<223> OTHER INFORMATION: Synthetically generated peptide

<400> SEQUENCE: 81

His Leu Phe Arg Ala Leu Leu Arg Leu Leu Arg His Leu Trp Arg Leu
1               5                   10                  15

Leu His Arg Ala
            20

<210> SEQ ID NO 82
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 82

His Leu Phe Arg Ala Leu His Arg Leu Leu Arg His Leu Trp Arg Leu
1               5                   10                  15

Leu His Arg Ala
            20

<210> SEQ ID NO 83
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 83

His Leu Phe Arg Ala Leu Arg Arg Leu Leu Arg His Leu Trp Arg Leu
1               5                   10                  15

Leu Arg Arg Ala
            20

<210> SEQ ID NO 84
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 84

His Leu Phe Arg His Leu Leu Arg Leu Leu Arg Arg Leu Trp His Leu
1               5                   10                  15

Leu His Arg Ala
            20

<210> SEQ ID NO 85
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 85

His Leu Phe Arg His Leu Leu Arg Leu Leu Arg His Leu Trp Arg His
1               5                   10                  15

Leu Leu Arg Ala
            20

<210> SEQ ID NO 86
<211> LENGTH: 20
```

```
<212> TYPE: PRT
<213> ORGANISM: Artificial Sequence
<220> FEATURE:
<223> OTHER INFORMATION: Synthetically generated peptide

<400> SEQUENCE: 86

Gly Leu Phe Arg Ala Leu Leu Arg Leu Leu Arg Ser Leu Trp Arg Leu
1               5                   10                  15

Leu Ser Arg Ala
            20

<210> SEQ ID NO 87
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 87

Gly Leu Phe Arg Ala Leu Leu Arg Leu Leu Arg Ser Leu Trp Arg Ser
1               5                   10                  15

Leu Leu Arg Ala
            20

<210> SEQ ID NO 88
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 88

Gly Leu Phe Arg Ala Leu Leu Arg Leu Leu Arg Ser Leu Trp Arg Ser
1               5                   10                  15

Leu Ser Arg Ala
            20

<210> SEQ ID NO 89
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 89

Gly Arg Ala Leu Leu Arg Leu Leu Arg Ser Leu Trp Arg Leu Leu Leu
1               5                   10                  15

Arg Ala

<210> SEQ ID NO 90
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 90

Gly Arg Ala Leu Leu Arg Leu Leu Arg Ser Leu Trp Arg Leu Leu Ser
1               5                   10                  15

Arg Ala

<210> SEQ ID NO 91
<211> LENGTH: 20
<212> TYPE: PRT
<213> ORGANISM: Artificial Sequence
```

```
<220> FEATURE:
<223> OTHER INFORMATION: Synthetically generated peptide

<400> SEQUENCE: 91

Gly Ala Phe Arg Ala Ala Leu Arg Leu Leu Arg Ser Leu Trp Arg Leu
 1               5                  10                  15

Leu Leu Arg Ala
         20

<210> SEQ ID NO 92
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 92

Gly Leu Phe Arg Ala Leu Leu Arg Leu Leu Arg Ser Leu Trp Arg Ala
 1               5                  10                  15

Arg Ala

<210> SEQ ID NO 93
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 93

Gly Ala Phe Arg Ala Ala Ala Arg Leu Leu Arg Ser Leu Trp Arg Leu
 1               5                  10                  15

Leu Leu Arg Ala
         20

<210> SEQ ID NO 94
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 94

Gly Ala Phe Arg Ala Ala Ala Arg Leu Leu Arg Ser Leu Trp Arg Ala
 1               5                  10                  15

Leu Leu Arg Ala
         20

<210> SEQ ID NO 95
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 95

Gly Leu Phe Arg Ala Arg Ala Leu Arg Ser Leu Trp Arg Ala Arg Ala
 1               5                  10                  15

<210> SEQ ID NO 96
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 96
```

```
Gly Ala Tyr Arg Ala Leu Arg Leu Leu Arg Ser Leu Trp Arg Leu
1               5                   10                  15

Leu Ser Arg Ala
            20

<210> SEQ ID NO 97
<211> LENGTH: 25
<212> TYPE: PRT
<213> ORGANISM: Artificial Sequence
<220> FEATURE:
<223> OTHER INFORMATION: Synthetically generated peptide

<400> SEQUENCE: 97

Gly Leu Phe Arg Ala Leu Leu Arg Leu Arg Ser Leu Trp Arg Leu
1               5                   10                  15

Leu Leu Arg Ala His His His His His
            20                  25

<210> SEQ ID NO 98
<211> LENGTH: 25
<212> TYPE: PRT
<213> ORGANISM: Artificial Sequence
<220> FEATURE:
<223> OTHER INFORMATION: Synthetically generated peptide

<400> SEQUENCE: 98

Arg Leu Phe Arg Ala Leu Leu Arg Leu Arg Ser Leu Trp Arg Leu
1               5                   10                  15

Leu Leu Arg Ala His His His His His
            20                  25

<210> SEQ ID NO 99
<211> LENGTH: 25
<212> TYPE: PRT
<213> ORGANISM: Artificial Sequence
<220> FEATURE:
<223> OTHER INFORMATION: Synthetically generated peptide

<400> SEQUENCE: 99

Arg Leu Phe Arg Ala Leu Leu Arg Leu Leu Arg Ser Leu Trp Arg Leu
1               5                   10                  15

Leu Arg Arg Ala His His His His His
            20                  25

<210> SEQ ID NO 100
<211> LENGTH: 25
<212> TYPE: PRT
<213> ORGANISM: Artificial Sequence
<220> FEATURE:
<223> OTHER INFORMATION: Synthetically generated peptide

<400> SEQUENCE: 100

His Leu Phe Arg Ala Leu Leu Arg Leu Leu Arg His Leu Trp Arg Leu
1               5                   10                  15

Leu Leu Arg Ala His His His His His
            20                  25

<210> SEQ ID NO 101
<211> LENGTH: 25
<212> TYPE: PRT
<213> ORGANISM: Artificial Sequence
<220> FEATURE:
<223> OTHER INFORMATION: Synthetically generated peptide

<400> SEQUENCE: 101
```

```
His His His His His Arg Leu Phe Arg Ala Leu Leu Arg Leu Leu Arg
  1               5                  10                  15

Ser Leu Trp Arg Leu Leu Leu Arg Ala
            20                  25

<210> SEQ ID NO 102
<211> LENGTH: 30
<212> TYPE: PRT
<213> ORGANISM: Artificial Sequence
<220> FEATURE:
<223> OTHER INFORMATION: Synthetically generated peptide

<400> SEQUENCE: 102

His His His His His Arg Leu Phe Arg Ala Leu Leu Arg Leu Leu Arg
  1               5                  10                  15

Ser Leu Trp Arg Leu Leu Leu Arg Ala His His His His His
            20                  25                  30

<210> SEQ ID NO 103
<211> LENGTH: 30
<212> TYPE: PRT
<213> ORGANISM: Artificial Sequence
<220> FEATURE:
<223> OTHER INFORMATION: Synthetically generated peptide

<400> SEQUENCE: 103

Arg Leu Phe Arg Ala Leu Leu Arg Leu Leu Arg Ser Leu Trp Arg Leu
  1               5                  10                  15

Leu Leu Arg Ala His His His His His His His His
            20                  25                  30
```